(12) United States Patent
Oden et al.

(10) Patent No.: US 12,378,209 B2
(45) Date of Patent: Aug. 5, 2025

(54) PROTEASE INHIBITORS

(71) Applicant: MEDIVIR AB, Huddinge (SE)

(72) Inventors: Lourdes Salvador Oden, Huddinge (SE); Magnus Nilsson, Huddinge (SE); Pia Kahnberg, Huddinge (SE); Bertil Samuelsson, Huddinge (SE); Urszula Grabowska, Huddinge (SE)

(73) Assignee: MEDIVIR AB, Huddinge (SE)

( * ) Notice: Subject to any disclaimer, the term of this patent is extended or adjusted under 35 U.S.C. 154(b) by 740 days.

(21) Appl. No.: 17/728,943

(22) Filed: Apr. 25, 2022

(65) Prior Publication Data

US 2022/0332690 A1      Oct. 20, 2022

Related U.S. Application Data

(60) Continuation of application No. 16/940,067, filed on Jul. 27, 2020, now Pat. No. 11,312,693, which is a
(Continued)

(30) Foreign Application Priority Data

Sep. 24, 2008    (GB) ..................... 0817424

(51) Int. Cl.
C07D 277/40    (2006.01)
C07D 491/048   (2006.01)
C07D 495/04    (2006.01)

(52) U.S. Cl.
CPC ....... C07D 277/40 (2013.01); C07D 491/048 (2013.01); C07D 495/04 (2013.01)

(58) Field of Classification Search
CPC . C07D 277/40; C07D 491/048; C07D 495/04
See application file for complete search history.

(56) References Cited

U.S. PATENT DOCUMENTS

| 7,893,067 B2 | 2/2011 | Nilsson et al. |
| 8,198,283 B2 | 6/2012 | Nilsson et al. |

(Continued)

FOREIGN PATENT DOCUMENTS

| WO | 1998050533 A1 | 11/1998 |
| WO | 2005055180 A1 | 6/2005 |

(Continued)

OTHER PUBLICATIONS

Biskobing, Expert Opinion on Investigational Drugs, vol. 12, p. 611-621 (2003).
Bodanszky, Peptide Chemistry, 2nd rev. ed., Springer-Verlag, Berlin, Germany, 1993.
Cai et al., Expert Opinion on Therapeutic Patents, vol. 15, p. 33-48 (2005).
Collet et al., Enantiomers, Racemates and Resolutions, John Wiley & Sons, Inc. 1981.
Delaisse et al., "Proteinases in bone resorption: obvious and less obvious roles", Clinica Chimica Acta, vol. 29, pp. 223-234 (2000).
Mehta, G. and Srinivas, K., "Synthetic Studies Towards Novel Terpenic Natural Products Kelsoene and Podman: Construction of the Complete 4-5-5-Fused Tricarbocyclic Core", Synlett, No. 5, pp. 555-556, 1999.
Skoumal et al., "Serum cathepsin K levels of patients with longstanding rheumatoid arthritis: correlation with radiological destruction", Arthritis Research & Therapy, vol. 7, pp. R65-R70 (2005).

(Continued)

*Primary Examiner* — Erich A Leeser

(74) *Attorney, Agent, or Firm* — Gorman IP Law, APC; Susan W. Gorman

(57) ABSTRACT

Compounds of the formula II:

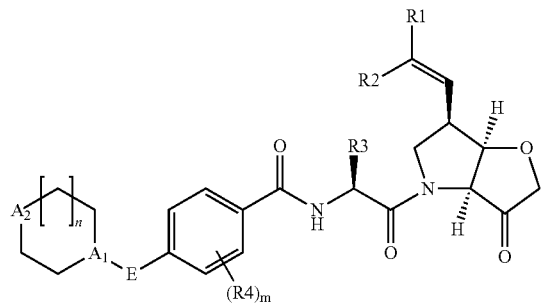

wherein
$R^1$ and $R^2$ are independently H, F or $CH_3$; or
$R^1$ forms an ethynyl bond and $R^2$ is H or $C_3$-$C_6$ cycloalkyl which is optionally substituted with one or two substituents independently selected from methyl, $CF_3$, OMe or halo;
$R^3$ is $C_1$-$C_3$ alkyl or $C_3$-$C_6$ cycloalkyl, either of which is optionally substituted with one or two methyl and/or a fluoro, trifluoromethyl or methoxy, when $R^3$ is $C_3$-$C_6$ cycloalkyl it may alternatively be gem subsituted with fluoro;
$R^4$ is methyl or fluoro; m is 0, 1 or 2;
E is a bond, or thiazolyl, optionally substituted with methyl or fluoro;
$A_1$ is CH or N,
$A_2$ is $CR^6R7$ or $NR^6$, provided at least one of $A_1$ and $A_2$ comprises N;
$R^6$ is H, $C_1$-$C_4$ alkyl, $C_1$-$C_4$ haloalkyl, $C_1$-$C_3$ alkyl-O-$C_1$-$C_3$ alkyl, or when $A_2$ is C, $R^6$ can also be $C_1$-$C_4$ alkoxy or F;
$R^7$ is H, $C_1$-$C_4$ alkyl or F
or a pharmaceutically acceptable salt, N-oxide or hydrate thereof, have utility in the treatment of disorders characterized by inappropriate expression or activation of cathepsin K, such as osteoporosis, osteoarthritis, rheumatoid arthritis or bone metastases.

1 Claim, 1 Drawing Sheet

Related U.S. Application Data continuation of application No. 16/449,850, filed on Jun. 24, 2019, now Pat. No. 10,723,709, which is a continuation of application No. 15/941,947, filed on Mar. 30, 2018, now Pat. No. 10,329,266, which is a continuation of application No. 15/667,292, filed on Aug. 2, 2017, now abandoned, which is a continuation of application No. 15/247,804, filed on Aug. 25, 2016, now abandoned, which is a continuation of application No. 14/940,817, filed on Nov. 13, 2015, now Pat. No. 9,428,517, which is a division of application No. 14/249,332, filed on Apr. 9, 2014, now Pat. No. 9,200,006, which is a continuation of application No. 13/831,267, filed on Mar. 14, 2013, now Pat. No. 8,735,395, which is a continuation of application No. 13/541,519, filed on Jul. 3, 2012, now Pat. No. 8,426,421, which is a division of application No. 12/739,489, filed as application No. PCT/EP2009/062406 on Sep. 24, 2009, now Pat. No. 8,242,119.

(56) References Cited

U.S. PATENT DOCUMENTS

| | | |
|---|---|---|
| 8,242,119 B2 | 8/2012 | Oden et al. |
| 8,426,421 B2 | 4/2013 | Nilsson et al. |
| 8,466,158 B2 | 6/2013 | Nilsson et al. |
| 8,735,395 B2 | 5/2014 | Nilsson et al. |
| 9,200,006 B2 | 12/2015 | Oden et al. |
| 2011/0077254 A1 | 3/2011 | Quibell et al. |
| 2011/0077264 A1 | 3/2011 | Galli et al. |

FOREIGN PATENT DOCUMENTS

| | | | | |
|---|---|---|---|---|
| WO | 2005056529 A1 | 6/2005 | | |
| WO | 2008007107 A1 | 1/2008 | | |
| WO | 2008007114 A1 | 1/2008 | | |
| WO | WO 2008/007107 | * | 1/2008 | ........... C07D 491/04 |
| WO | 2005066180 A9 | 9/2008 | | |
| WO | 2008114054 A1 | 9/2008 | | |
| WO | 2009000877 A1 | 12/2008 | | |
| WO | 2009087379 A2 | 7/2009 | | |
| WO | 2010034790 A1 | 4/2010 | | |

OTHER PUBLICATIONS

Srinivas et al., "Synthetic Studies Towards Novel Terpenic Natural Products Kelsoene and Produran: Construction of the Complete 4-5-5-Fused Tricarbocyclic Core," Synlett, vol. 5, p. 555-556, 1999.
Truong et al., Practical and Efficient Route to (S)-gamma-Fluoroleucine, Synlett, 2005; (8) 1279-1280.
Tschaen et al., An Improved Procedure for Aromatic Cyanation, Synth. Commun., 1994; 24(6) 887-890.

* cited by examiner

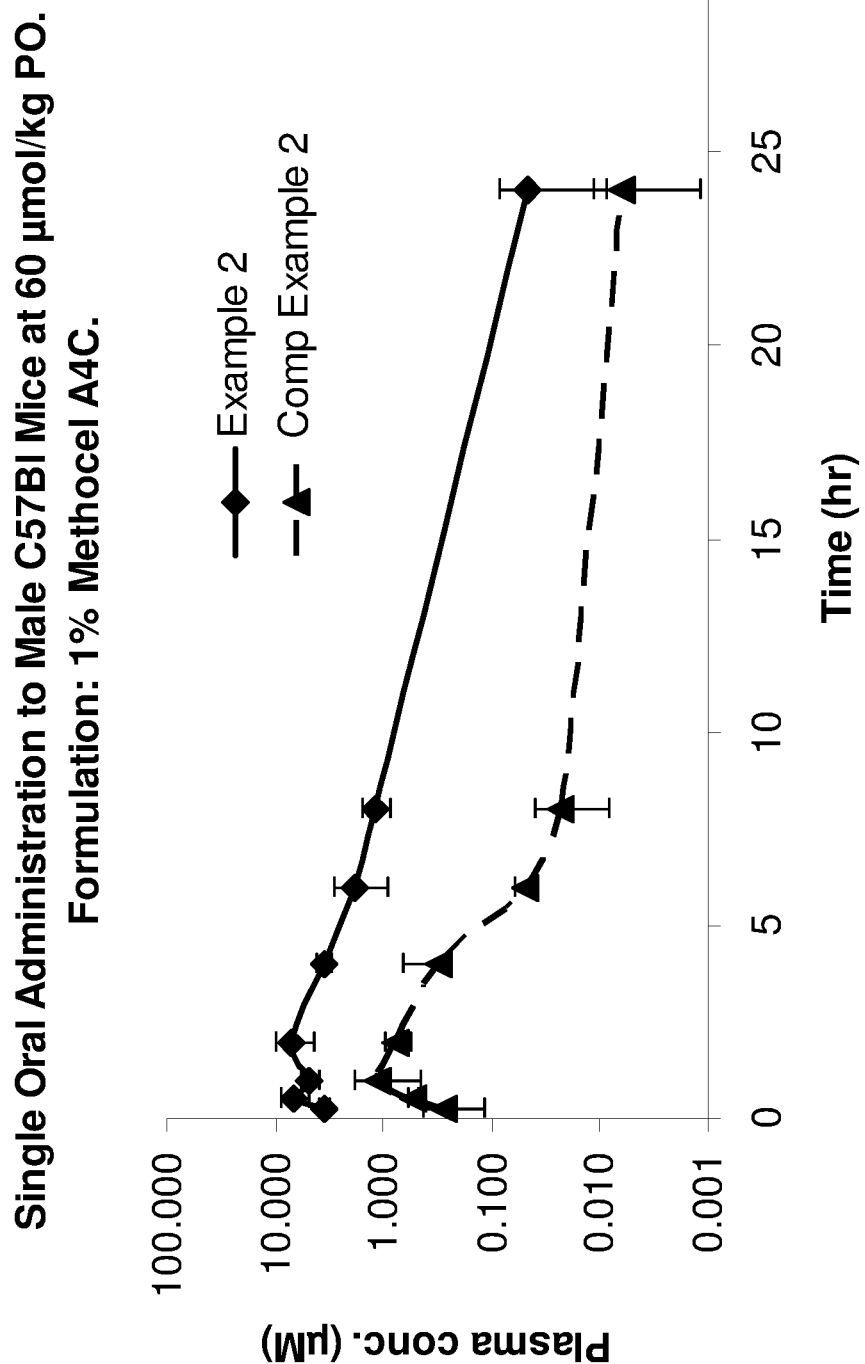

PROTEASE INHIBITORS

This application is a Continuation of pending application Ser. No. 16/940,067 filed on Jul. 27, 2020, which is a Continuation of application Ser. No. 16/449,850 filed on Jun. 24, 2019 now U.S. Pat. No. 10,723,709, which is a Continuation of application Ser. No. 15/941,947 filed on Mar. 30, 2018, now U.S. Pat. No. 10,329,266, which is a Continuation of abandoned application Ser. No. 15/667,292 filed on Aug. 2, 2017, which is a Continuation of abandoned application Ser. No. 15/247,804 filed on Aug. 25, 2016, which is a Continuation of Ser. No. 14/940,817 filed on Nov. 13, 2015, now U.S. Pat. No. 9,428,517, which is a Divisional of application Ser. No. 14/249,332 filed on Apr. 9, 2014, now U.S. Pat. No. 9,200,006, which is a Continuation of Ser. No. 13/831,267 filed on Mar. 14, 2013, now U.S. Pat. No. 8,735,395, which is a Continuation of Ser. No. 13/541,519 filed on Jul. 3, 2012, now U.S. Pat. No. 8,426,421, which is a Divisional of application Ser. No. 12/739,489 filed on Oct. 26, 2010, now U.S. Pat. No. 8,242,119 and for which priority is claimed under 35 U.S.C. § 120. This application claims priority of application Ser. No. 12/739,489 is the National Phase of PCT International Application No. PCT/EP2009/062406 filed on Sep. 24, 2009 under 35 U.S.C. § 371. This application also claims priority of Application No. 0817424.5 filed in Great Britain on Sep. 24, 2008 under 35 U.S.C. § 119. The entire contents of each of the above-identified applications are hereby incorporated by reference in their entirety.

FIELD OF THE INVENTION

This invention relates to inhibitors of cysteine proteases, especially those of the papain superfamily. The invention provides novel compounds useful in the prophylaxis or treatment of disorders stemming from misbalance of physiological proteases such as cathepsin K.

DESCRIPTION OF THE RELATED ART

The papain superfamily of cysteine proteases is widely distributed in diverse species including mammals, invertebrates, protozoa, plants and bacteria. A number of mammalian cathepsin enzymes, including cathepsins B, F, H, K, L, O and S, have been ascribed to this superfamily, and inappropriate regulation of their activity has been implicated in a number of metabolic disorders including arthritis, muscular dystrophy, inflammation, glomerulonephritis and tumour invasion. Pathogenic cathepsin like enzymes include the bacterial gingipains, the malarial falcipains I, II, Ill et seq and cysteine proteases from *Pneumocystis carinii, Trypanosoma cruzei* and *brucei, Crithidia fusiculata, Schistosoma* spp.

The inappropriate regulation of cathepsin K has been implicated in a number of disorders including osteoporosis, gingival diseases such as gingivitis and periodontitis, Paget's disease, hypercalcaemia of malignancy and metabolic bone disease. In view of its elevated levels in chondroclasts of osteoarthritic synovium, cathepsin K is implicated in diseases characterised by excessive cartilage or matrix degradation, such as osteoarthritis and rheumatoid arthritis.

It is likely that treatment of bone and cartilage disorders such as osteoarthritis and osteoporosis will require life-long administration of a cathepsin K inhibitor, often to a patient population within or nearing the geriatric phase. This places unusually high requirements on the ease of administration of drugs intended for such disorders. For example attempts are underway to stretch the dosage regimes of the current osteoporosis drugs of the bisphosphonate class to weekly or longer administration regimes to aid compliance. However, even with improved dosing, other side effects of the bisphosphonates remain. Bisphosphonates block bone turnover rather than attenuate it as a cathepsin K inhibitor does. For healthy bone it is important to maintain the remodelling process which bisphosphonates block completely. In addition, bis-phosphonates have a very long half-life in bone so if effects such as osteonecrosis of the jaw manifest themselves, it is impossible to remove the bisphosphonate from the bone. In contrast, cathepsin K inhibitors typically have a fast onset and off rate mode of action, which means that if a problem was to be identified, dosing could be halted and there would be no build up of the inhibitor in the bone matrix.

There is thus a desire for alternative osteoporosis and osteoarthritis drugs with superior pharmacokinetic and/or pharmacodynamic properties.

International patent application no WO2008/007107 discloses compounds of the formula

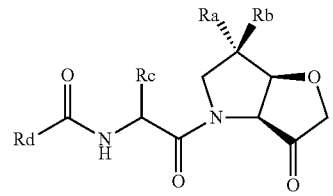

where Rd is a substituted monocyclic ring, Rc is branched alkyl or cycloalkyl and Ra and Rb are a variety of groups including H, methyl, ethyl, ether, thioether, amine, sulphonate etc. The only compounds which are prepared have H or methoxy at this position.

There remains a need in the art for potent inhibitors of cathepsin K. Of particular benefit are inhibitors of cathepsin K which show selectivity for cathepsin K over other cathepsins (e.g. selectivity over cathepsin S and/or cathepsin L). Potent inhibitors of cathepsin K which demonstrate properties such as high permeability and/or advantageous metabolic profiles may be expected to be of great value in a clinical setting. Cathepsin K related indications such as osteoporosis or arthritis presuppose protracted periods of administration and therefore it is desirable that the compounds have minimal toxicity or genotoxicity.

BRIEF DESCRIPTION OF THE INVENTION

According to the present invention, there is provided a compound of formula II:

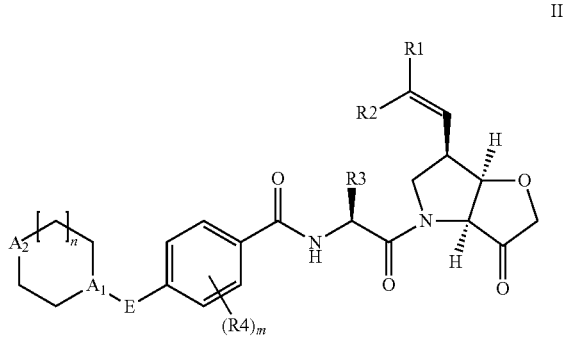

wherein

R$^1$ and R$^2$ are independently H, F or CH$_3$; or

R$^1$ forms an ethynyl bond and R$^2$ is H or C$_3$-C$_6$ cycloalkyl which is optionally substituted with one or two substituents independently selected from methyl, CF$_3$, OMe or halo;

R$^3$ is C$_1$-C$_3$ alkyl or C$_3$-C$_6$ cycloalkyl, either of which is optionally substituted with one or two methyl and/or a fluoro, trifluoromethyl or methoxy, when R$^3$ is C$_3$-C$_6$ cycloalkyl it may alternatively be gem subsituted with fluoro;

R$^4$ is methyl or fluoro; m is 0, 1 or 2;

E is thiazolyl, optionally substituted with methyl or fluoro;

A$_1$ is CH or N,

A$_2$ is CR$^6$R$^7$ or NR$^6$, provided at least one of A$_1$ and A$_2$ comprises N;

R$^6$ is H, C$_1$-C$_4$ alkyl, C$_1$-C$_4$ haloalkyl, C$_1$-C$_3$ alkyl-O-C$_1$-C$_3$ alkyl, or when A$_2$ is C, R$^6$ can also be C$_1$-C$_4$ alkoxy or F;

R$^7$ is H, C$_1$-C$_4$ alkyl or F or a pharmaceutically acceptable salt, N-oxide or hydrate thereof.

It will be appreciated that the compounds of the invention can exist as hydrates, such as those of the partial formulae:

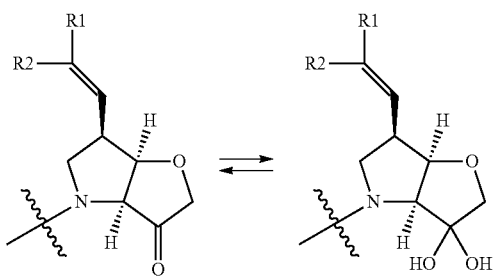

and the invention extends to all such alternative forms.

In certain embodiments of the invention, R$^1$ and R$^2$ are both H, both methyl or more preferably both F.

In other embodiments of the invention R$^1$, together with the olefin depicted in Formula II defines an ethynyl bond, for example acetylene when R$^2$ is H.

In other embodiments of the invention, R$^1$, together with the olefin depicted in Formula II defines an ethynyl bond and R$^2$ is a cycloalkyl moiety, such as cyclopentyl, more preferably cyclobutyl and most preferably cyclopropyl. The cycloalkyl is optionally substituted at any position, including the 1-position with 1, where valance allows 2 substituents selected from methyl, OMe, halo (such as fluoro) or CF$_3$.

An embodiment of the invention thus defines compounds of the formula:

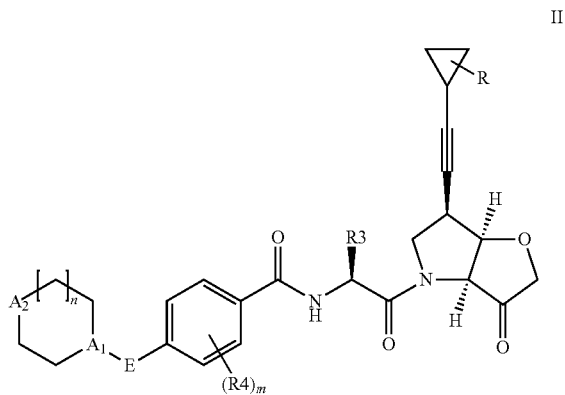

II

Where A$_2$, n, A$_1$, E, R$^4$, m and R$^3$ are as defined above or any of the preferments defined below and R is H, methyl, CF$_3$, OMe or halo, such as fluoro, located at any of the 1, 2 or 3 positions.

Suitably R$^3$ is C$_1$-C$_3$ alkyl or C$_3$-C$_6$ cycloalkyl, either of which is optionally substituted with one or two methyl and/or a fluoro, trifluoromethyl or methoxy.

Representative values for cycloalkyl for R$^3$ include cyclopropyl, cyclobutyl and especially cyclopentyl or cyclohexyl, any of which being substitued with fluoro or gem fluoro. Gem-fluoro at the 2 position of a cyclopropyl, the 3 position of cyclobutyl or cyclopentyl or the 4 position of cyclopropyl is often convenient. Gem-fluoro at the 4 position of cyclohexyl is also often convenient.

In one embodiment of the invention R$^3$ represents the side chain of leucine. In a second embodiment of the invention R$^3$ represents the side chain of isoleucine. In a third embodiment of the invention R$^3$ represents the side chain of cyclohexylglycine. In a fourth embodiment of the invention R$^3$ represents the side chain of cyclopentylglycine. In a fifth embodiment of the invention, R$^3$ represents the side chain of O-methylthreonine. In a fifth embodiment of the invention R$^3$ represents the side chain of 4-fluoroleucine. In a sixth embodiment of the invention R$^3$ represents the side chain of 3-methoxyvaline.

Currently preferred values of R$^3$ include those embodied by the partial structures:

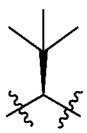

and especially

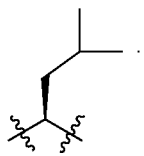

In one embodiment of the invention m represents 2. Of particular interest are compounds wherein m represents 1. Still further embodiments of the invention have m as 0, especially when the adjacent thiazolyl is substituted with Me or preferably F.

$R^4$ suitably represents methyl or fluoro, especially fluoro. If m is 2, it is currently preferred that each $R^4$ is the same.

When m represents 1, $R^4$ is suitably positioned as shown by the partial structure:

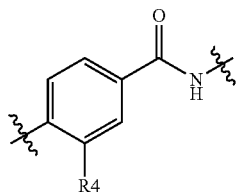

As defined above, E is thiazolyl, which is optionally substituted with methyl or more preferably fluoro. The preferred orientation of the thiazolyl ring is:

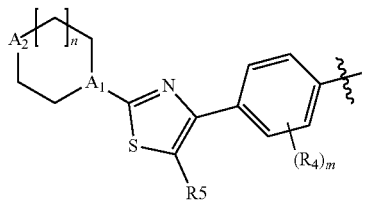

where $R^5$ is H methyl or fluoro.

The ring containing $A_1$ and $A_2$ is a saturated, nitrogen-containing ring of 5 or 6 ring atoms. Representative rings thus include pyrrolidin-1-yl, pyrrolidin-3-yl, piperazin-1-yl, piperidin-4-yl and piperidine-1-yl. The ring is conveniently substituted, for example with alkyl or haloalkyl, typically methyl or propyl or trifluromethyl. Alternatively the ring is substituted with an ether such as methoxymethyl- or methoxyethyl-. When $A^2$ is carbon, the ring can alternatively be substitued with alkoxy such as methoxy, or fluoro, especially gem-fluoro.

A favoured embodiment of the invention has the formula IIa:

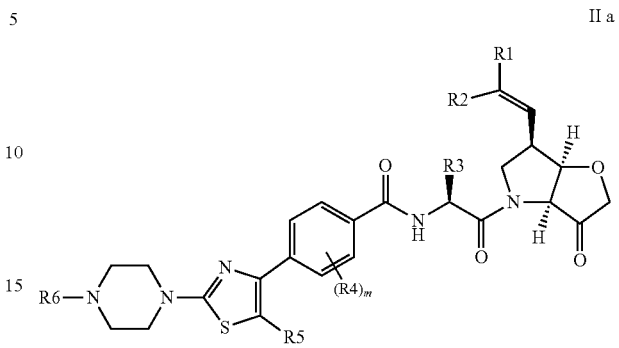

IIa wherein
$R^1$ and $R^2$ are independently H, F or $CH_3$; or
$R^1$ forms an ethenyl bond and $R^2$ is H, $C_3$-$C_6$ cycloalkyl, optionally substituted with one or two substituents selected from Me, $CF_3$, OMe or halo (such as fluoro);
$R^3$ is branched $C_2$-$C_6$ alkyl or $C_3$-$C_6$ cycloalkyl, either of which is substituted with halo or trifluoromethyl;
$R^4$ is methyl or fluoro; m is 0 or 1 or 2;
$R^5$ is H, methyl or fluoro;
$R^6$ is $C_1$-$C_4$ alkyl;
or a pharmaceutically acceptable salt, N-oxide or hydrate thereof (collectively referred to herein as compounds of the invention).

$R^5$ is preferably fluoro, especially when m is 0. The remaining preferments are as defined above in relation to Formula II. References to formula II below are understood to include the corresponding embodiments of formula IIa.

Representative embodiments of formula II, in which the —C≡CR¹R² moiety is acetylene include:
N-[1-(6-ethynyl-3-oxo-hexahydro-furo[3,2-b]pyrrol-4-carbonyl)-3-methyl-butyl]-4-[2-(4-methyl-piperazin-1-yl)-thiazol-4-yl]-benzamide;
N-[1-(6-ethynyl-3-oxo-hexahydro-furo[3,2-b]pyrrol-4-yl)-1-cyclohexyl-2-oxo-ethyl]-4-[2-(4-methyl-piperazin-1-yl)-thiazol-4-yl]-benzamide;
N-[1-(6-ethynyl-3-oxo-hexahydro-furo[3,2-b]pyrrol-4-yl)-1-cyclopentyl-2-oxo-ethyl]-4-[2-(4-methyl-piperazin-1-yl)-thiazol-4-yl]-benzamide;
N-[1-(6-ethynyl-3-oxo-hexahydro-furo[3,2-b]pyrrol-4-carbonyl)-2-methyl-butyl]-4-[2-(4-methyl-piperazin-1-yl)-thiazol-4-yl]-benzamide;
N-[1-(6-ethynyl-3-oxo-hexahydro-furo[3,2-b]pyrrol-4-carbonyl)-3-methyl-butyl]-4-[5-methyl-2-(4-methyl-piperazin-1-yl)-thiazol-4-yl]-benzamide;
N-[1-(6-ethynyl-3-oxo-hexahydro-furo[3,2-b]pyrrol-4-yl)-1-cyclohexyl-2-oxo-ethyl]-4-[5-methyl-2-(4-methyl-piperazin-1-yl)-thiazol-4-yl]-benzamide;
N-[1-(6-ethynyl-3-oxo-hexahydro-furo[3,2-b]pyrrol-4-yl)-1-cyclohexyl-2-oxo-ethyl]-4-[5-methyl-2-(4-methyl-piperazin-1-yl)-thiazol-4-yl]-benzamide;
N-[1-(6-ethynyl-3-oxo-hexahydro-furo[3,2-b]pyrrol-4-carbonyl)-2-methyl-butyl]-4-5-methyl-2-(4-methyl-piperazin-1-yl)-thiazol-4-yl]-benzamide;
N-[1-(6-ethynyl-3-oxo-hexahydro-furo[3,2-b]pyrrol-4-carbonyl)-3-methyl-butyl]-4-[5-fluoro-2-(4-methyl-piperazin-1-yl)-thiazol-4-yl]benzamide;
N-[1-(6-ethynyl-3-oxo-hexahydro-furo[3,2-b]pyrrol-4-yl)-1-cyclohexyl-2-oxo-ethyl]-4-[5-fluoro-2-(4-methyl-piperazin-1-yl)-thiazol-4-yl]-benzamide;
N-[1-(6-ethynyl-3-oxo-hexahydro-furo[3,2-b]pyrrol-4-yl)-1-cyclopentyl-2-oxo-ethyl]-4-[5-fluoro-2-(4-methyl-piperazin-1-yl)-thiazol-4-yl]-benzamide N-[1-(6-ethynyl-3-oxo-hexahydro-furo[3,2-b]pyrrol-4-carbonyl)-2-methyl-butyl]-4-[5-fluoro-2-(4-methyl-piperazin-1-yl)-thiazol-4-yl]-benzamide;

N-[1-(6-ethynyl-3-oxo-hexahydro-furo[3,2-b]pyrrol-4-carbonyl)-3-methyl-butyl]-3-fluoro-4-[2-(4-methyl-piperazin-1-yl)-thiazol-4-yl]-benzamide;

N-[1-(6-ethynyl-3-oxo-hexahydro-furo[3,2-b]pyrrol-4-yl)-1-cyclohexyl-2-oxo-ethyl]-3-fluoro-4-[2-(4-methyl-piperazin-1-yl)-thiazol-4-yl]benzamide;

N-[1-(6-ethynyl-3-oxo-hexahydro-furo[3,2-b]pyrrol-4-yl)-1-cyclopentyl-2-oxo-ethyl]-3-fluoro-4-[2-(4-methyl-piperazin-1-yl)-thiazol-4-yl]-benzamide;

N-[1-(6-ethynyl-3-oxo-hexahydro-furo[3,2-b]pyrrol-4-carbonyl)-2-methyl-butyl]-3-fluoro-4-[2-(4-methyl-piperazin-1-yl)-thiazol-4-yl]-benzamide and pharmaceutically acceptable salts, N-oxides and hydrates thereof.

Further representative embodiments of formula II, in which W and $R^2$ are methyl include:

N-[1-(6-(dimethylvinyl)-3-oxo-hexahydro-furo[3,2-b]pyrrol-4-carbonyl)-3-methyl-butyl]-4-[2-(4-methyl-piperazin-1-yl)-thiazol-4-yl]-benzamide;

N-[1-(6-(dimethylvinyl)-3-oxo-hexahydro-furo[3,2-b]pyrrol-4-yl)-1-cyclohexyl-2-oxo-ethyl]-4-[2-(4-methyl-piperazin-1-yl)-thiazol-4-yl]benzamide;

N-[1-(6-(dimethylvinyl)-3-oxo-hexahydro-furo[3,2-b]pyrrol-4-yl)-1-cyclopentyl-2-oxo-ethyl]-4-[2-(4-methyl-piperazin-1-yl)-thiazol-4-yl]-benzamide;

N-[1-(6-(dimethylvinyl)-3-oxo-hexahydro-furo[3,2-b]pyrrol-4-carbonyl)-2-methyl-butyl]-4-[2-(4-methyl-piperazin-1-yl)-thiazol-4-yl]-benzamide;

N-[1-(6-(dimethylvinyl)-3-oxo-hexahydro-furo[3,2-b]pyrrol-4-carbonyl)-3-methyl-butyl]-4-[5-methyl-2-(4-methyl-piperazin-1-yl)-thiazol-4-yl]-benzamide;

N-[1-(6-(dimethylvinyl)-3-oxo-hexahydro-furo[3,2-b]pyrrol-4-yl)-1-cyclohexyl-2-oxo-ethyl]-4-[5-methyl-2-(4-methyl-piperazin-1-yl)-thiazol-4-yl]-benzamide;

N-[1-(6-(dimethylvinyl)-3-oxo-hexahydro-furo[3,2-b]pyrrol-4-yl)-1-cyclohexyl-2-oxo-ethyl]-4-[5-methyl-2-(4-methyl-piperazin-1-yl)-thiazol-4-yl]-benzamide;

N-[1-(6-(dimethylvinyl)-3-oxo-hexahydro-furo[3,2-b]pyrrol-4-carbonyl)-2-methylbutyl]-4-5-methyl-2-(4-methyl-piperazin-1-yl)-thiazol-4-yl]-benzamide;

N-[1-(6-(dimethylvinyl)-3-oxo-hexahydro-furo[3,2-b]pyrrol-4-carbonyl)-3-methyl-butyl]-4-[5-fluoro-2-(4-methyl-piperazin-1-yl)-thiazol-4-yl]-benzamide;

N-[1-(6-(dimethylvinyl)-3-oxo-hexahydro-furo[3,2-b]pyrrol-4-yl)-1-cyclohexyl-2-oxo-ethyl]-4-[5-fluoro-2-(4-methyl-piperazin-1-yl)-thiazol-4-yl]-benzamide;

N-[1-(6-(dimethylvinyl)-3-oxo-hexahydro-furo[3,2-b]pyrrol-4-yl)-1-cyclopentyl-2-oxo-ethyl]-4-[5-fluoro-2-(4-methyl-piperazin-1-yl)-thiazol-4-yl]-benzamide N-[1-(6-(dimethylvinyl)-3-oxo-hexahydro-furo[3,2-b]pyrrol-4-carbonyl)-2-methyl-butyl]-4-[5-fluoro-2-(4-methyl-piperazin-1-yl)-thiazol-4-yl]-benzamide;

N-[1-(6-(dimethylvinyl)-3-oxo-hexahydro-furo[3,2-b]pyrrol-4-carbonyl)-3-methyl-butyl]-3-fluoro-4-[2-(4-methyl-piperazin-1-yl)-thiazol-4-yl]-benzamide;

N-[1-(6-(dimethylvinyl)-3-oxo-hexahydro-furo[3,2-b]pyrrol-4-yl)-1-cyclohexyl-2-oxo-ethyl]-3-fluoro-4-[2-(4-methyl-piperazin-1-yl)-thiazol-4-yl]-benzamide;

N-[1-(6-(dimethylvinyl)-3-oxo-hexahydro-furo[3,2-b]pyrrol-4-yl)-1-cyclopentyl-2-oxo-ethyl]-3-fluoro-4-[2-(4-methyl-piperazin-1-yl)-thiazol-4-yl]-benzamide;

N-[1-(6-(dimethylvinyl)-3-oxo-hexahydro-furo[3,2-b]pyrrol-4-carbonyl)-2-methyl-butyl]-3-fluoro-4-[2-(4-methyl-piperazin-1-yl)-thiazol-4-yl]-benzamide and pharmaceutically acceptable salts, N-oxides and hydrates thereof.

Further preferred embodiments of formula II, in which $R^1$ and $R^2$ are F include N-[1-(6-(difluorovinyl)-3-oxo-hexahydro-furo[3,2-b]pyrrol-4-carbonyl)-3-methyl-butyl]-4-[2-(4-methyl-piperazin-1-yl)-thiazol-4-yl]-benzamide;

N-[1-(6-(difluorovinyl)-3-oxo-hexahydro-furo[3,2-b]pyrrol-4-yl)-1-cyclohexyl-2-oxo-ethyl]-4-[2-(4-methyl-piperazin-1-yl)-thiazol-4-yl]-benzamide;

N-[1-(6-(difluorovinyl)-3-oxo-hexahydro-furo[3,2-b]pyrrol-4-yl)-1-cyclopentyl-2-oxo-ethyl]-4-[2-(4-methyl-piperazin-1-yl)-thiazol-4-yl]benzamide;

N-[1-(6-(difluorovinyl)-3-oxo-hexahydro-furo[3,2-b]pyrrol-4-carbonyl)-2-methyl-butyl]-4-[2-(4-methyl-piperazin-1-yl)-thiazol-4-yl]-benzamide;

N-[1-(6-(difluorovinyl)-3-oxo-hexahydro-furo[3,2-b]pyrrol-4-carbonyl)-3-methyl-butyl]-4-[5-methyl-2-(4-methyl-piperazin-1-yl)-thiazol-4-yl]-benzamide;

N-[1-(6-(difluorovinyl)-3-oxo-hexahydro-furo[3,2-b]pyrrol-4-yl)-1-cyclohexyl-2-oxo-ethyl]-4-[5-methyl-2-(4-methyl-piperazin-1-yl)-thiazol-4-yl]-benzamide;

N-[1-(6-(difluorovinyl)-3-oxo-hexahydro-furo[3,2-b]pyrrol-4-yl)-1-cyclohexyl-2-oxo-ethyl]-4-[5-methyl-2-(4-methyl-piperazin-1-yl)-thiazol-4-yl]-benzamide;

N-[1-(6-(difluorovinyl)-3-oxo-hexahydro-furo[3,2-b]pyrrol-4-carbonyl)-2-methyl-butyl]-4-5-methyl-2-(4-methyl-piperazin-1-yl)-thiazol-4-yl]-benzamide;

N-[1-(6-(difluorovinyl)-3-oxo-hexahydro-furo[3,2-b]pyrrol-4-carbonyl)-3-methyl-butyl]-4-[5-fluoro-2-(4-methyl-piperazin-1-yl)-thiazol-4-yl]-benzamide;

N-[1-(6-(difluorovinyl)-3-oxo-hexahydro-furo[3,2-b]pyrrol-4-yl)-1-cyclohexyl-2-oxo-ethyl]-4-[5-fluoro-2-(4-methyl-piperazin-1-yl)-thiazol-4-yl]-benzamide;

N-[1-(6-(difluorovinyl)-3-oxo-hexahydro-furo[3, 2-b]pyrrol-4-yl)-1-cyclopentyl-2-oxo-ethyl]-4-[5-fluoro-2-(4-methyl-piperazin-1-yl)-thiazol-4-yl]-benzamide N-[1-(6-(difluorovinyl)-3-oxo-hexahydro-furo[3,2-b]pyrrol-4-carbonyl)-2-methyl-butyl]-4-[5-fluoro-2-(4-methyl-piperazin-1-yl)-thiazol-4-yl]-benzamide;

N-[1-(6-(difluorovinyl)-3-oxo-hexahydro-furo[3,2-b]pyrrol-4-carbonyl)-3-methyl-butyl]-3-fluoro-4-[2-(4-methyl-piperazin-1-yl)-thiazol-4-yl]-benzamide;

N-[1-(6-(difluorovinyl)-3-oxo-hexahydro-furo[3,2-b]pyrrol-4-yl)-1-cyclohexyl-2-oxo-ethyl]-3-fluoro-4-[2-(4-methyl-piperazin-1-yl)-thiazol-4-yl]-benzamide;

N-[1-(6-(difluorovinyl)-3-oxo-hexahydro-furo[3,2-b]pyrrol-4-yl)-1-cyclopentyl-2-oxo-ethyl]-3-fluoro-4-[2-(4-methyl-piperazin-1-yl)-thiazol-4-yl]-benzamide;

N-[1-(6-(difluorovinyl)-3-oxo-hexahydro-furo[3, 2-b]pyrrol-4-carbonyl)-2-methyl-butyl]-3-fluoro-4-[2-(4-methyl-piperazin-1-yl)-thiazol-4-yl]benzamide and pharmaceutically acceptable salts, N-oxides and hydrates thereof.

Further preferred embodiments of formula II, in which $R^1$ is an ethynyl bond and $R^2$ is cyclopropyl include:

N-[1-(6-(cyclopropylethynyl)-3-oxo-hexahydro-furo[3,2-b]pyrrol-4-carbonyl)-3-methyl-butyl]-4-[2-(4-methyl-piperazin-1-yl)-thiazol-4-yl]benzamide;

N-[1-(6-(cyclopropylethynyl)-3-oxo-hexahydro-furo[3,2-b]pyrrol-4-yl)-1-cyclohexyl-2-oxo-ethyl]-4-[2-(4-methyl-piperazin-1-yl)-thiazol-4-yl]- benzamide;

N-[1-(6-(cyclopropylethynyl)-3-oxo-hexahydro-furo[3,2-b]pyrrol-4-yl)-1-cyclopentyl-2-oxo-ethyl]-4-[2-(4-methyl-piperazin-1-yl)-thiazol-4-yl]- benzamide;

N-[1-(6-(cyclopropylethynyl)-3-oxo-hexahydro-furo[3,2-b]pyrrol-4-carbonyl)-2-methyl-butyl]-4-[2-(4-methyl-piperazin-1-yl)-thiazol-4-yl]-benzamide;
N-[1-(6-(cyclopropylethynyl)-3-oxo-hexahydro-furo[3,2-b]pyrrol-4-carbonyl)-3-methyl-butyl]-4-[5-methyl-2-(4-methyl-piperazin-1-yl)-thiazol-4-yl]-benzamide;
N-[1-(6-(cyclopropylethynyl)-3-oxo-hexahydro-furo[3,2-b]pyrrol-4-yl)-1-cyclohexyl-2-oxo-ethyl]-4-[5-methyl-2-(4-methyl-piperazin-1-yl)- thiazol-4-yl]-benzamide;
N-[1-(6-(cyclopropylethynyl)-3-oxo-hexahydro-furo[3,2-b]pyrrol-4-yl)-1-cyclohexyl-2-oxo-ethyl]-4-[5-methyl-2-(4-methyl-piperazin-1-yl)-thiazol- 4-yl]-benzamide;
N-[1-(6-(cyclopropylethynyl)-3-oxo-hexahydro-furo[3,2-b]pyrrol-4-carbonyl)-2-methyl-butyl]-4-5-methyl-2-(4-methyl-piperazin-1-yl)-thiazol-4-yl]-benzamide;
N-[1-(6-(cyclopropylethynyl)-3-oxo-hexahydro-furo[3,2-b]pyrrol-4-carbonyl)-3-methyl-butyl]-4-[5-fluoro-2-(4-methyl-piperazin-1-yl)-thiazol-4-yl]-benzamide;
N-[1-(6-(cyclopropylethynyl)-3-oxo-hexahydro-furo[3,2-b]pyrrol-4-yl)-1-cyclohexyl-2-oxo-ethyl]-4-[5-fluoro-2-(4-methyl-piperazin-1-yl)-thiazol- 4-yl]-benzamide;
N-[1-(6-(cyclopropylethynyl)-3-oxo-hexahydro-furo[3,2-b]pyrrol-4-yl)-1-cyclopentyl-2-oxo-ethyl]-4-[5-fluoro-2-(4-methyl-piperazin-1-yl)- thiazol-4-yl]-benzamide;
N-[1-(6-(cyclopropylethynyl)-3-oxo-hexahydro-furo[3,2-b]pyrrol-4-carbonyl)-2-methyl-butyl]-4-[5-fluoro-2-(4-methyl-piperazin-1-yl)-thiazol-4-yl]-benzamide;
N-[1-(6-(cyclopropylethynyl)-3-oxo-hexahydro-furo[3,2-b]pyrrol-4-carbonyl)-3-methyl-butyl]-3-fluoro-4-[2-(4-methyl-piperazin-1-yl)-thiazol-4-yl]-benzamide;
N-[1-(6-(cyclopropylethynyl)-3-oxo-hexahydro-furo[3,2-b]pyrrol-4-yl)-1-cyclohexyl-2-oxo-ethyl]-3-fluoro-4-[2-(4-methyl-piperazin-1-yl)-thiazol- 4-yl]-benzamide;
N-[1-(6-(cyclopropylethynyl)-3-oxo-hexahydro-furo[3,2-b]pyrrol-4-yl)-1-cyclopentyl-2-oxo-ethyl]-3-fluoro-4-[2-(4-methyl-piperazin-1-yl)- thiazol-4-yl]-benzamide;
N-[1-(6-(cyclopropylethynyl)-3-oxo-hexahydro-furo[3,2-b]pyrrol-4-carbonyl)-2-methyl-butyl]-3-fluoro-4-[2-(4-methyl-piperazin-1-yl)-thiazol-4-yl]-benzamide and pharmaceutically acceptable salts, N-oxides and hydrates thereof.

The $C_1$-$C_n$ alkyl definition of $R^6$ or $R^7$ is meant to include both branched and unbranched alkyl moieties containing between one and n carbon atoms in total. Examples of such $R^6$ groups or $R^7$ are methyl, ethyl, propyl (n-propyl and isopropyl), butyl (n-butyl, isobutyl, tert-butyl and sec-butyl). One $R^6$ group of particular interest is methyl. A second $R^6$ group of particular interest is propyl (especially n-propyl). As $R^3$ is optionally substituted with one or two methyl groups, this moiety may also define a branched alkyl chain of up to 5 C atoms.

In some embodiments of the invention $A_1$ is N.

Additional aspects of the invention include a pharmaceutical composition comprising a compound as defined above and a pharmaceutically acceptable carrier or diluent therefor.

A further aspect of the invention is the use of a compound as defined above in the manufacture of a medicament for the treatment of disorders mediated by cathepsin K, such as:
osteoporosis,
gingival diseases (such as gingivitis and periodontitis),
Paget's disease,
hypercalcaemia of malignancy,
metabolic bone disease,
diseases characterised by excessive cartilage or matrix degradation (such as
osteoarthritis and rheumatoid arthritis),
bone cancers including neoplasia,
pain (especially chronic pain).

Additionally provided is a method for the treatment or prevention of a disorder mediated by cathepsin K comprising the administration of a safe and effective amount of a compound of the invention for the purpose of treating or preventing said disorder which is mediated by cathepsin K.

Also provided is a compound of the invention for the treatment or prevention of a disorder mediated by cathepsin K.

Further, there is provided as an aspect of the invention novel intermediates (as described herein) which may be of use in the preparation of the compounds of the invention.

In particular there is provided a compound of the formula:

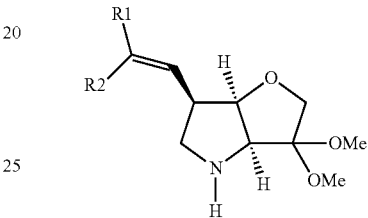

or an N-protected derivative thereof (e.g. Boc, CBz, or Fmoc-protected). Also provided by the invention is the corresponding 1,3-dioxolane protected analogue and N-protected derivatives thereof (e.g. Boc- CBz, or Fmoc protected). Particularly favoured embodiments of this building block have both R' and $R^2$ as fluoro, or both methyl or the —C═C($R^1$)$R^2$ moiety is acetylene or cyclopropylethylene.

A further novel intermediate of the invention is has the formula:

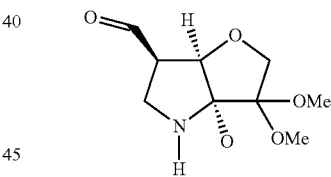

or the corresponding 1,3-dioxolane protected analogue, in each case wherein the N function is optionally protected with a conventional protecting group such as Boc, CBz or Fmoc.

The compounds of the invention can form salts which form an additional aspect of the invention. Appropriate pharmaceutically acceptable salts of the compounds of Formula II include salts of organic acids, especially carboxylic acids, including but not limited to acetate, trifluoroacetate, lactate, gluconate, citrate, tartrate, maleate, malate, pantothenate, isethionate, adipate, alginate, aspartate, benzoate, butyrate, digluconate, cyclopentanate, glucoheptanate, glycerophosphate, oxalate, heptanoate, hexanoate, fumarate, nicotinate, palmoate, pectinate, 3-phenylpropionate, picrate, pivalate, proprionate, tartrate, lactobionate, pivolate, camphorate, undecanoate and succinate, organic sulphonic acids such as methanesulphonate, ethanesulphonate, 2-hydroxy-ethane sulphonate, camphorsulphonate, 2-napthalenesulphonate, benzenesulphonate, p-chlorobenzenesulphonate and p-toluenesulphonate; and inorganic acids such as hydrochloride, hydrobromide, hydroiodide, sulphate, bisulphate, hemisulphate, thiocyanate, persulphate, phosphoric and sulphonic acids.

The compounds of the invention may in some cases be isolated as the hydrate. Hydrates are typically prepared by recrystallisation from an aqueous/organic solvent mixture using organic solvents such as dioxin, tetrahydrofuran or methanol. Hydrates can also be generated in situ by administration of the corresponding ketone to a patient.

The N-oxides of compounds of the invention can be prepared by methods known to those of ordinary skill in the art. For example, N-oxides can be prepared by treating an unoxidized form of the compound of the invention with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compounds of the invention can be prepared from the N-oxide of an appropriate starting material.

Examples of N-oxides of the invention include those with the partial structures:

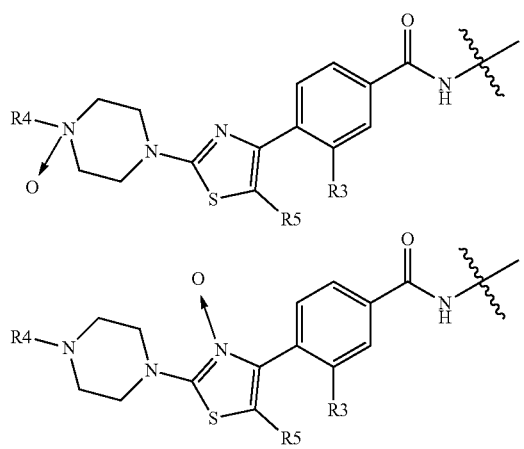

Compounds of the invention in unoxidized form can be prepared from N-oxides of the corresponding compounds of the invention by treating with a reducing agent (e.g., sulfur, sulfur dioxide, triphenyl phosphine, lithium borohydride, sodium borohydride, phosphorus bichloride, tribromide, or the like) in an suitable inert organic solvent (e.g., acetonitrile, ethanol, aqueous dioxane, or the like) at 0 to 80° C.

It should be noted that the radical positions on any molecular moiety used in the definitions may be anywhere on such moiety as long as it is chemically stable.

Radicals used in the definitions of the variables include all possible isomers unless otherwise indicated. For instance butyl includes t-butyl, i-butyl, n-butyl etc.

When any variable occurs more than one time in any constituent, each definition is independent.

Unless otherwise mentioned or indicated, the chemical designation of a compound encompasses the mixture of all possible stereochemically isomeric forms, which said compound may possess. Said mixture may contain all diastereomers and/or enantiomers of the basic molecular structure of said compound. All stereochemically isomeric forms of the compounds of the present invention both in pure form or mixed with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term "stereoisomerically pure" concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms "enantiomerically pure" and "diastereomerically pure" should be understood in a similar way, but then having regard to the enantiomeric excess, and the diastereomeric excess, respectively, of the mixture in question.

Compounds of the invention can be prepared as their individual stereoisomers by reacting a racemic mixture of the compound with an optically active resolving agent to form a pair of diastereoisomeric compounds, separating the diastereomers and recovering the optically pure enantiomer. While resolution of enantiomers can be carried out using covalent diasteromeric derivatives of compounds of Formula II, dissociable complexes are preferred (e.g., crystalline; diastereoisomeric salts). Diastereomers have distinct physical properties (e.g., melting points, boiling points, solubilities, reactivity, etc.) and can be readily separated by taking advantage of these dissimilarities. The diastereomers can be separated by chromatography, for example HPLC or, preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques Andre Collet, Samuel H. Wilen, Enantiomers, Racemates and Resolutions, John Wiley & Sons, Inc. (1981).

The compounds of formula II or any subgroup of formula II as defined herein include radioisotopes or radiomarked compounds, wherein one or more of the atoms is replaced by an isotope of that atom, i.e. an atom having the same atomic number as, but an atomic mass different from, the one(s) typically found in nature. Examples of isotopes that may be incorporated into the compounds of formula I or any subgroup of formula I, include but are not limited to isotopes of hydrogen, such as $^2$H and $^3$H (also denoted D for deuterium and T for tritium respectively), carbon, such as $^{11}$C, $^{13}$C and $^{14}$C, nitrogen, such as $^{13}$N and $^{15}$N, oxygen, such as $^{15}$O, $^{17}$O and $^{18}$O, phosphorus, such as $^{31}$P and $^{32}$P, sulphur, such as $^{35}$S, fluorine, such as $^{18}$F, chlorine, such as $^{36}$Cl, bromine such as $^{76}$Br, $^{76}$Br, $^{77}$Br and $^{82}$Br, and iodine, such as 123I, 124I, 125I and $^{131}$I.

The choice of isotope included in an isotope-labelled compound will depend on the specific application of that compound. For example, for drug or substrate tissue distribution assays, compounds wherein a radioactive isotope such as $^3$H or $^{14}$C is incorporated will generally be most useful. For radio-imaging applications, for example positron emission tomography (PET) a positron emitting isotope such as $^{11}$C, $^{18}$F, $^{13}$N or $^{15}$O will be useful. The incorporation of a heavier isotope, such as deuterium, i.e. $^2$H, may provide greater metabolic stability to a compound of formula I or any subgroup of formula I, which may result in, for example, an increased in vivo half life of the compound or reduced dosage requirements.

For synthetic convenience it will generally be preferred that the compounds of formula II are in the natural isotopic state.

Isotopically labelled compounds of formula I or any subgroup of formula II can be prepared by processes analogous to those described in the Schemes and/or Examples herein below by using the appropriate isotopically labelled reagent or starting material instead of the corresponding non-isotopically labelled reagent or starting material, or by conventional techniques known to those skilled in the art.

It will be appreciated that the invention extends to prodrugs, solvates, complexes and other forms releasing a compound of the invention in vivo.

While it is possible for the active agent to be administered alone, it is preferable to present it as part of a pharmaceutical formulation. Such a formulation will comprise the above defined active agent together with one or more acceptable carriers/excipients and optionally other therapeutic ingredients. The carrier(s) must be acceptable in the sense of being compatible with the other ingredients of the formulation and not deleterious to the recipient.

The formulations include those suitable for rectal, nasal, topical (including buccal and sublingual), vaginal or parenteral (including subcutaneous, intramuscular, intravenous and intradermal) administration, but preferably the formulation is an orally administered formulation.

The formulations may conveniently be presented in unit dosage form, e.g. tablets and sustained release capsules, and may be prepared by any methods well known in the art of pharmacy.

Such methods include the step of bringing into association the above defined active agent with the carrier. In general, the formulations are prepared by uniformly and intimately bringing into association the active agent with liquid carriers or finely divided solid carriers or both, and then if necessary shaping the product. The invention extends to methods for preparing a pharmaceutical composition comprising bringing a compound of Formula II or its pharmaceutically acceptable salt in conjunction or association with a pharmaceutically acceptable carrier or vehicle. If the manufacture of pharmaceutical formulations involves intimate mixing of pharmaceutical excipients and the active ingredient in salt form, then it is often preferred to use excipients which are non-basic in nature, i.e. either acidic or neutral.

Formulations for oral administration in the present invention may be presented as discrete units such as capsules, cachets or tablets each containing a predetermined amount of the active agent; as a powder or granules; as a solution or a suspension of the active agent in an aqueous liquid or a non-aqueous liquid; or as an oil-in-water liquid emulsion or a water in oil liquid emulsion and as a bolus etc.

With regard to compositions for oral administration (e.g. tablets and capsules), the term suitable carrier includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropyl-methylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate stearic acid, silicone fluid, talc waxes, oils and colloidal silica. Flavouring agents such as peppermint, oil of wintergreen, cherry flavouring or the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may be optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

The appropriate dosage for the compounds or formulations of the invention will depend upon the indication and the patient and is readily determined by conventional animal trials. Dosages providing intracellular (for inhibition of physiological proteases of the papain superamily) concentrations of the order 0.01-100 uM, more preferably 0.01-10 uM, such as 0.1-25 uM are typically desirable and achievable.

Compounds of the invention are prepared by a variety of solution and solid phase chemistries.

The compounds are typically prepared as building blocks reflecting the P1, P2 and P3 moieties of the end product inhibitor. Without in any way wishing to be bound by theory, or the ascription of tentative binding modes for specific variables, the notional concepts P1, P2 and P3 as used herein are provided for convenience only and have substantially their conventional Schlecter & Berger meanings and denote those portions of the inhibitor believed to fill the S1, S2, and S3 subsites respectively of the enzyme, where S1 is adjacent the cleavage site and S3 remote from the cleavage site. Compounds defined by Formula II are intended to be within the scope of the invention, regardless of binding mode.

Broadly speaking the P1 building block will have the formula:

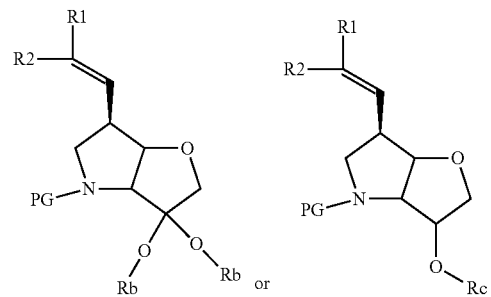

wherein $R^1$ and $R^2$ are as defined above, the two Rb groups define a ketal, such as the bis methyl ketal or together define a cyclic ketal such as 1,3-dioxolane;

and Rc is an hydroxy protecting group. Less commonly Rc is H or represents the keto function of the end-product inhibitor in cases where the P1 building block as the ketone is elongated with P2 and P3.

WO05/066180 describes the preparation of intermediates towards the above P1 building blocks, including:

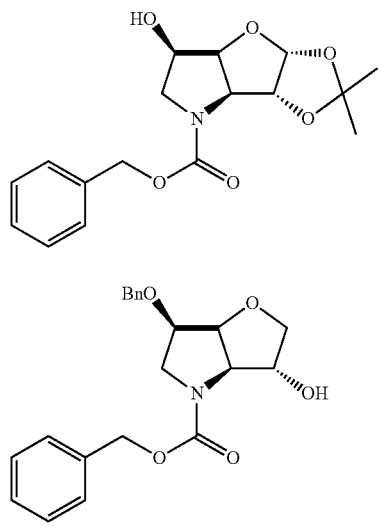

The first stage in the synthesis of compounds of the invention is typically the preparation in solution of a functionalized P1 building block. Scheme 1 illustrates a route to a convenient 6-aldehyde intermediate.

Scheme 1

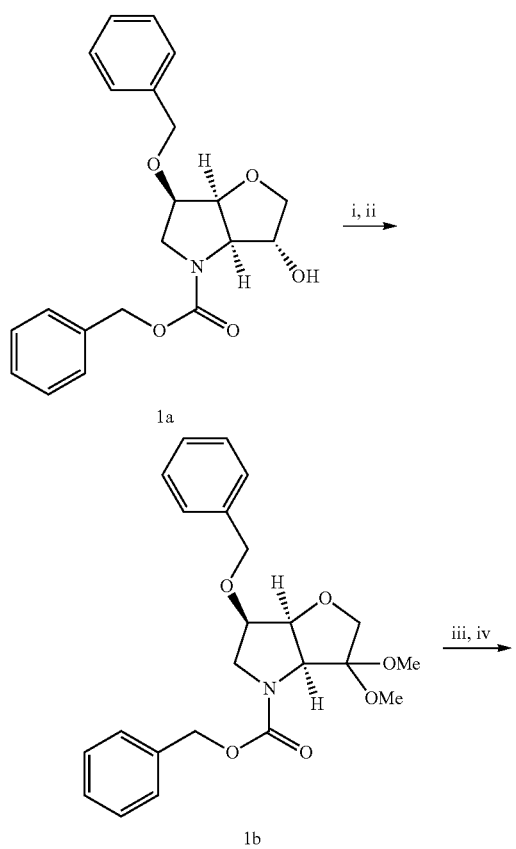

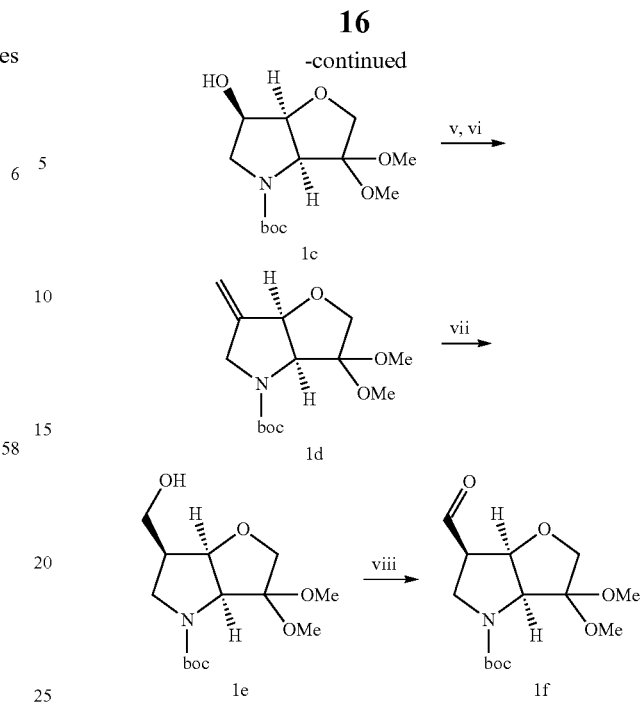

i) Dess-Martin Periodinane, DCM; ii) Trimethylorthoformate, pTs, MeOH; iii) Pd(OH)$_2$, H$_2$, MeOH; iv) Boc$_2$O, 10% Na$_2$CO$_3$, v) Dess-Martin Periodinane, DCM; vi) 1) CH$_3$PPh$_3$Br, KOtBu, THF; vii) 1) 9-BBN-H, THF, 2) NaBO$_3$, H$_2$O, THF; viii) Dess-Martin Periodinane, DCM.

The starting bicyclic alcohol (1a) can be prepared as described in WO05/066180. Oxidation of the hydroxy function for example with Dess-Martin periodinane followed by transformation of the afforded keto function into a dimethyl ketal effected by treatment with trimethyl orthoformate in the presence of an acid like p-toluenesulphonic acid provides the ketal (1b).

Removal of the Cbz and benzyl protecting groups effected for instance by hydrogenolysis using a catalyst like Pd(OH)2 or the like, followed by boc protection of the afforded free amine provides the alcohol (1c). Oxidation of the afforded free alcohol using for instance Dess-Martin periodinane in a solvent like dichloromethane followed by a Wittig reaction using methyl triphenylphosphinium bromide in the presence of KOt.Bu or the like provides the olefin (1d).

Hydroxylation of the double bond effected for example by treatment with 9-BBN-H, provides the primary alcohol (1e) which subsequently can be oxidized to the corresponding aldehyde (1f) using any suitable oxidation method such as treatment with Dess-Martin periodinane or the like.

Scheme 2 illustrates a typical procedure for a 6-acetylene P1 building block commencing from the 6-aldehyde intermediate of Scheme 1.

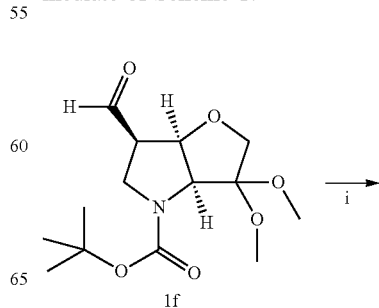

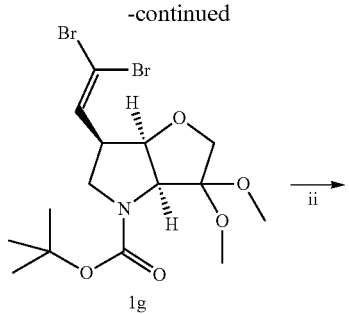

1g

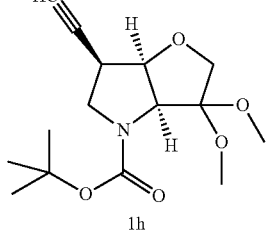

1h i) CBr₄, PPh₃ CH₂Cl₂, 0° C., ii) nBuLi, THF, -78 C.

The C-6 acetylene building block 1h is prepared as shown in Scheme 2. Essentially, the acetylene 1h is readily prepared from the aldehyde precursor 1f by the two step Corey-Fuchs methodology via the corresponding 1,1-dibromoolefin 1g. Aldehyde 1f is treated with triphenylphosphinecarbondibromide, for example generated from Ph₃PCH₂Cl₂ and CBr₄, at 0° C. to afford the dibromoalkene 1g. Subsequent treatment of the dibromide in an organic solvent such as THF at reduced temperature, typically -78° C. with n-butyl lithium affords on work-up, the acetylene 1h, generally in good yield. A number of conventional N-protecting groups could be used instead of the Boc group shown here. In addition, the dimethylketal can be replaced by a number of standard ketone protecting groups including cyclic ketals or, less commonly, the building block could be built up with the active keto functionality in place, prior to coupling.

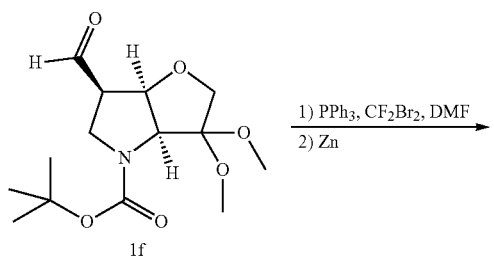

1f

1) PPh₃, CF₂Br₂, DMF
2) Zn

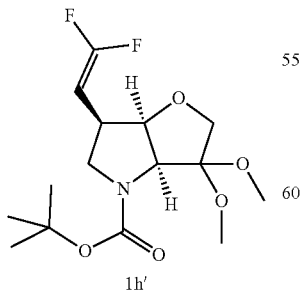

1h'

Compounds of formula II, where R¹ and/or R² define a fluorovinyl substituent are prepared by adding a fluoromethyl halide, such as dibromodifluoromethane to a solution of triphenylphosphine in an organic solvent such as DMF for example at 0° C. under an inert atmosphere. The solution is stirred for a short period of time (such 0.5 hrs) and then the aldehyde 1f and zinc powder are slowly added. After an hour at room temperature the reaction can be quenched by addition of aqueous NaHCO₃ to yield a protected P1 building block 1h' (represented above the N-Boc and dimethyl acetal, but other conventional protecting groups can be envisaged).

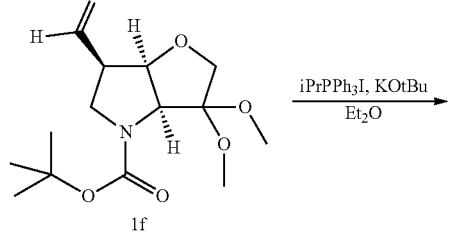

1f iPrPPh₃I, KOtBu
————————→
Et₂O

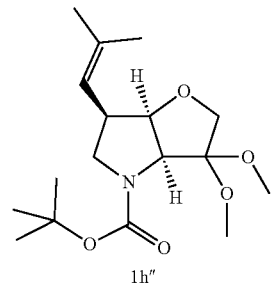

1h"

Compounds of formula II, wherein R¹ and/or R² define a methylated vinyl substituent can be prepared by a Wittig reaction. For example, potassium tert-butoxide is added to a suspension of an activated alkyl, such as isopropyl triphenylphosphonium iodide in diethyl ether. After approx. 2 hrs aldehyde 1f, dissolved in a solvent such as diethylether is added to the solution. After stirring (eg 1 hr) the reaction can be quenched with aqueous ammonium chloride to yield the vinyl building block 1h" (illustrated above as the dimethyl-vinyl). Although the scheme has been

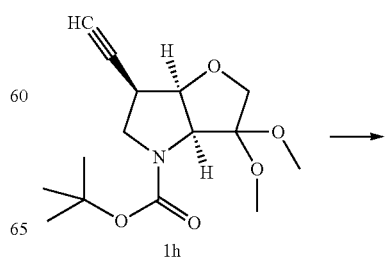

1h

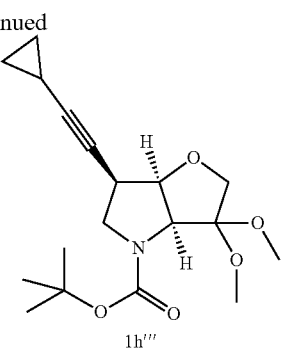

1h''' depicted with the N-Boc and dimethyl acetal protecting groups, it will be apparent that other conventional protecting groups can be envisaged.

Compounds of formula II wherein $R^2$ is an optionally substituted cycloalkyl group may be prepared by alkylation of the corresponding ethynyl building block. In the example above 1h is treated with a strong base, for example sodium amide, to get the acetylide, which is subsequently reacted with the appropriate cycloalkyl halide to yield the building block 1h''' (in the example above cyclopropyl chloride, but other activated cycloalkyls will also be effective). Alternatively the acetylene function can be extended by reaction with $ClCH_2CH_2Br$ followed by treatment with a base to form a cyclopropyl ring. Although the scheme has been depicted with the N-Boc and dimethyl acetal protecting groups, it will be apparent that other conventional protecting groups can be envisaged.

Typically to get to the final compound, the appropriate P1 building blocks such 1h, 1h', 1h" or 1h''', is N-deprotected in a conventional fashion, such as treatment with acetyl chloride in methanol to remove an N-Boc protecting group. With the subsequent free amine, the P2 residue is introduced, eg via BocP2-OH using standard coupling conditions such as HATU, DIPEA in DMF. The terminal Boc protection is again removed with acetyl chloride in methanol and the P3 residue introduced via P3-OH using standard coupling conditions such as HATU, DIPEA in DMF. Finally the dimethylketal protection is removed with TFA to afford the required final compound.

Elongation is typically carried out in the presence of a suitable coupling agent e.g., benzotriazole-1-yloxytrispyrrolidinophosphonium hexafluorophosphate (PyBOP), O-benzotriazol-1-yl-N,N,N',N'-tetramethyl-uronium hexafluorophosphate (HBTU), O-(7-azabenzotriazol-1-yl)-1,1,3,3-tetramethyl-uronium hexafluorophosphate (HATU), 1-(3-dimethylaminopropyl)-3-ethylcarbodiimide hydrochloride (EDC), or 1,3-dicyclohexyl carbodiimide (DCC), optionally in the presence of 1-hydroxybenzotriazole (HOBT), and a base such as N,N-diisopropylethylamine, triethylamine, N-methylmorpholine, and the like. The reaction is typically carried out at 20 to 30° C., preferably at about 25° C., and requires 2 to 24 h to complete. Suitable reaction solvents are inert organic solvents such as halogenated organic solvents (e.g., methylene chloride, chloroform, and the like), acetonitrile, N,N-dimethylformamide, ethereal solvents such as tetrahydrofuran, dioxane, and the like.

Alternatively, the above elongation coupling step can be carried out by first converting the P3/P2 building block into an active acid derivative such as succinimide ester and then reacting it with the P1 amine. The reaction typically requires 2 to 3 h to complete. The conditions utilized in this reaction depend on the nature of the active acid derivative. For example, if it is an acid chloride derivative, the reaction is carried out in the presence of a suitable base (e.g. triethylamine, diisopropylethylamine, pyridine, and the like). Suitable reaction solvents are polar organic solvents such as acetonitrile, N,N-dimethylformamide, dichloromethane, or any suitable mixtures thereof.

The P2 building block is typically an N-protected amino acid such as L-leucine, L-isoleucine, O-methyl-L-threonine, L-3-hydroxyvaline, 4-fluoroleucine, L-cyclopentylglycine or L-cyclohexylglycine, and P3 typically comprises a capping group such as a benzoic acid derivative with, eg, the N-alkyl-piperazinyl-E moiety already introduced or provided with a synthon therefor in the para position.

The suitably protected individual building blocks can first be prepared and subsequently coupled together, preferably in the sequence P2+P1→P2-P1 followed by N-alkylpiperazinyl-E-benzoic acid*+P2-P1→N-alkylpiperazinyl-E-benzoate-P2-P1, where * denotes an activated form, in order to minimise racemisation at P2.

Coupling between two amino acids, an amino acid and a peptide, or two peptide fragments can be carried out using standard coupling procedures such as the azide method, mixed carbonic-carboxylic acid anhydride (isobutyl chloroformate) method, carbodiimide (dicyclohexylcarbodiimide, diisopropylcarbodiimide, or water-soluble carbodiimide) method, active ester (p-nitrophenyl ester, N-hydroxysuccinic imido ester) method, Woodward reagent K-method, carbonyldiimidazole method, phosphorus reagents or oxidation-reduction methods. Some of these methods (especially the carbodiimide method) can be enhanced by adding 1-hydroxybenzotriazole or 4-DMAP. These coupling reactions can be performed in either solution (liquid phase) or solid phase.

More explicitly, the coupling step involves the dehydrative coupling of a free carboxyl of one reactant with the free amino group of the other reactant in the present of a coupling agent to form a linking amide bond. Descriptions of such coupling agents are found in general textbooks on peptide chemistry, for example, M. Bodanszky, "Peptide Chemistry", 2nd rev ed., Springer-Verlag, Berlin, Germany, (1993) hereafter simply referred to as Bodanszky, the contents of which are hereby incorporated by reference. Examples of suitable coupling agents are N,N'-dicyclohexylcarbodiimide, 1-hydroxybenzotriazole in the presence of N,N'-dicyclohexylcarbodiimide or N-ethyl-N'-[ (3-dimethylamino)propyl] carbodiimide. A practical and useful coupling agent is the commercially available (benzotriazol-1-yloxy)tris-(dimethylamino) phosphonium hexafluorophosphate, either by itself or in the present of 1-hydroxybenzotriazole or 4-DMAP. Another practical and useful coupling agent is commercially available 2-(1H-benzotriazol-1-yl)-N,N,N', N'-tetramethyluronium tetrafluoroborate. Still another practical and useful coupling agent is commercially available O-(7-azabenzotriazol-1-yl)-N,N,N',N'-tetramethyluronium hexafluorophosphate.

The coupling reaction is conducted in an inert solvent, e.g. dichloromethane, acetonitrile or dimethylformamide. An excess of a tertiary amine, e. g. diisopropylethylamine, N-methylmorpholine, N-methylpyrrolidine or 4-DMAP is added to maintain the reaction mixture at a pH of about 8. The reaction temperature usually ranges between 0° C. and 50° C. and the reaction time usually ranges between 15 min and 24 h.

The functional groups of the constituent non-natural amino acids generally must be protected during the coupling reactions to avoid formation of undesired bonds. The protecting groups that can be used are listed in Greene, "Protective Groups in Organic Chemistry", John Wiley & Sons, New York (1981) and "The Peptides: Analysis, Synthesis, Biology", Vol. 3, Academic Press, New York (1981), hereafter referred to simply as Greene, the disclosures of which are hereby incorporated by reference.

The alpha-carboxyl group of the C-terminal residue is usually protected as an ester that can be cleaved to give the carboxylic acid. Protecting groups that can be used include 1) alkyl esters such as methyl, trimethylsilyl and t-butyl, 2) aralkyl esters such as benzyl and substituted benzyl, or 3) esters that can be cleaved by mild base or mild reductive means such as trichloroethyl and phenacyl esters.

The alpha-amino group of each amino acid to be coupled is typically N- protected. Any protecting group known in the art can be used. Examples of such groups include: 1) acyl groups such as formyl, trifluoroacetyl, phthalyl, and p-toluenesulfonyl; 2) aromatic carbamate groups such as benzyloxycarbonyl (Cbz or Z) and substituted benzyloxycarbonyls, and 9-fluorenylmethyloxycarbonyl (Fmoc); 3) aliphatic carbamate groups such as tertbutyloxycarbonyl (Boc), ethoxycarbonyl, diisopropylmethoxy-carbonyl, and allyloxycarbonyl; 4) cyclic alkyl carbamate groups such as cyclopentyloxycarbonyl and adamantyloxycarbonyl;

5) alkyl groups such as triphenylmethyl and benzyl; 6) trialkylsilyl such as trimethylsilyl; and 7) thiol containing groups such as phenylthiocarbonyl and dithiasuccinoyl. The preferred alpha-amino protecting group is either Boc or Fmoc. Many amino acid derivatives suitably protected for peptide synthesis are commercially available.

The alpha-amino protecting group is typically cleaved prior to the next coupling step. When the Boc group is used, the methods of choice are trifluoroacetic acid, neat or in dichloromethane, or HCl in dioxane or in ethyl acetate. The resulting ammonium salt is then neutralized either prior to the coupling or in situ with basic solutions such as aqueous buffers, or tertiary amines in dichloromethane or acetonitrile or dimethylformamide. When the Fmoc group is used, the reagents of choice are piperidine or substituted piperidine in dimethylformamide, but any secondary amine can be used. The deprotection is carried out at a temperature between 0° C. and room temperature usually 20-22° C.

Once the inhibitor sequence is completed any remaining protecting groups are removed in whatever manner is dictated by the choice of protecting groups. These procedures are well known to those skilled in the art.

P2 building blocks in the form of N-protected L-amino acids are readily available commercially, for example L-leucine, L-isoleucine, L-cyclohexylglycine, O-methyl-L threonine and others are available commercially with a number of protecting group variants such as CBz, Boc or Fmoc. Other variants of R³ are easily prepared from commercially available starting materials. For example compounds wherein R³ is —C(CH₃)₂OCH₃ can be prepared by reacting CBz protected (S)-(+)-2-amino-3-hydroxy-3-methylbutanoic acid with 3,3-dimethoxy-hexahydro-furo(3,2b)pyrrole to form the desired P2-P1 unit. The P2 side chain alcohol can now be methylated using methyliodide under conventional sodium hydride, imidazole, THF conditions to obtain the desired P2 without substantial racemisation of the alpha centre. This P2-P1 moiety can now be carried through the synthesis as described herein, namely CBz removal and coupling.

WO05/565299 describes the preparation of a gamma-fluoroleucine P2 building block. An alternative synthesis of Fmoc and N-Boc-gammafluoroleucine building blocks is shown in Truong et al Syn. Lett. 2005 no 8 1278-1280.

The preparation of P3 building blocks are described in W005/066180, W008/007114 or readily prepared by analogous methods. For example, Scheme E below shows the preparation of a P3 building block wherein E is a fluoro-substituted thiazolyl:

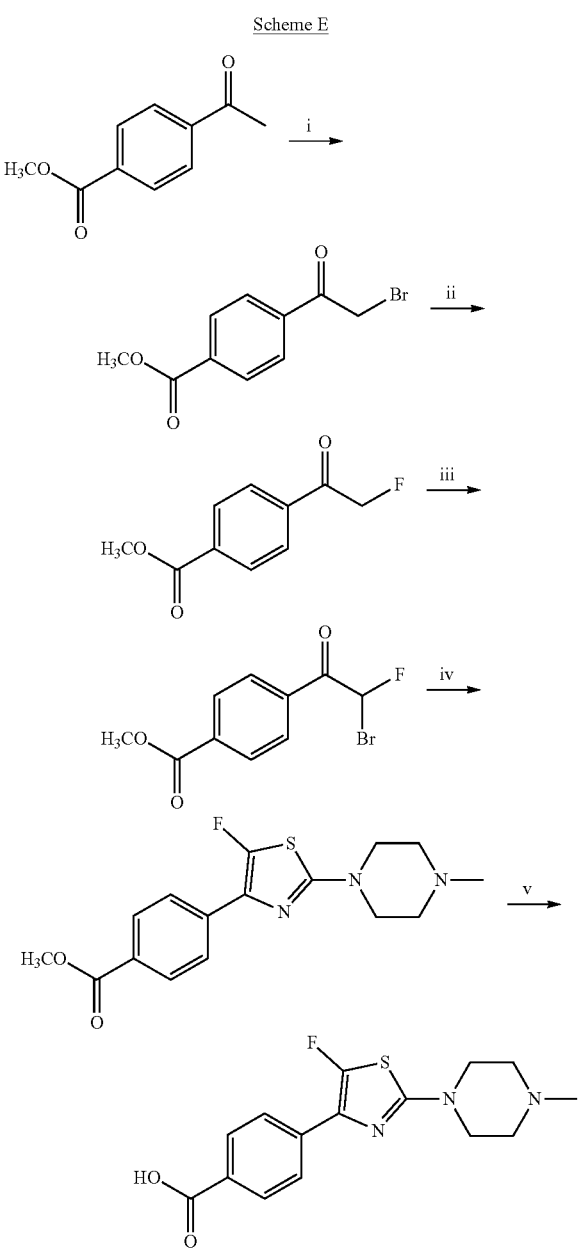

Scheme E i. HOAc, Br₂, RT, 2 h, 55% yield; ii. KF, 18-crown-6, CH₃CN, 90° C., 16 h, 31% yield; iii. HOAc, Br₂, 45° C., 4 h, 100% yield; iv. 4-methylpiperazine-1-carbothioamide, ethanol, 70° C., 2 h, 74% yield, v. LiOH, THF, H₂O, RT, 16 h, 79% yield.

Synthesis of 4-[5-fluoro-2-(4-methyl-piperazin-1-yl)-thiazol-4-yl]-benzoic Acid

The starting material, methyl 4-acetylbenzoate, is commercially available. Bromination at the α-position to the ketone is achieved with bromine in acetic acid to provide the desired 4-(2-bromo-acetyl)-benzoic acid methyl ester. Subsequent treatment of 4-(2-bromo-acetyl)-benzoic acid methyl ester with potassium fluoride in the presence of 18-crown-6 at 90° C., provides 4-(2-fluoro-acetyl)-benzoic acid methyl ester after column chromatography. Repeated bromination at the α-position to the ketone is achieved with bromine in acetic acid to provide the desired 4-(2-bromo-2-fluoro-acetyl)-benzoic acid methyl ester. Formation of the thiazole is typically carried out by heating 4-(2-bromo-2-fluoro-acetyl)-benzoic acid methyl ester with 4-methylpiperazine-1-carbothioamide at 70° C. for 2 hours. On cooling, the desired 4-[5-fluoro-2-(4-methyl-piperazin-1-yl)-thiazol-4-yl]-benzoic acid methyl ester precipitates out. Deprotection of the methyl ester is carried out using a lithium hydroxide solution and the desired acid, 4-[5-fluoro-2-(4-methyl-piperazin-1-yl)-thiazol-4-yl]-benzoic acid is generally obtained in good yield as the dihydrochloride salt on workup with hydrochloric acid.

The term "N-protecting group" or "N-protected" as used herein refers to those groups intended to protect the N-terminus of an amino acid or peptide or to protect an amino group against undesirable reactions during synthetic procedures. Commonly used N-protecting groups are disclosed in Greene, "Protective Groups in Organic Synthesis" (John Wiley & Sons, New York, 1981), which is hereby incorporated by reference. N-protecting groups include acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl, and the like, carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butoxycarbonyl, diisopropylmethoxycarbonyl, isopropyloxycarbonyl, ethoxycarbonyl, methoxycarbonyl, allyloxycarbonyl, 2,2,2-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl, and the like; alkyl groups such as benzyl, triphenylmethyl, benzyloxymethyl and the like; and silyl groups such as trimethylsilyl and the like. Favoured N-protecting groups include formyl, acetyl, benzoyl, pivaloyl, t-butylacetyl, phenylsulfonyl, benzyl (bz), t-butoxycarbonyl (BOC) and benzyloxycarbonyl (Cbz).

Hydroxy and/or carboxy protecting groups are also extensively reviewed in Greene ibid and include ethers such as methyl, substituted methyl ethers such as methoxymethyl, methylthiomethyl, benzyloxymethyl, t-butoxymethyl, 2-methoxyethoxymethyl and the like, silyl ethers such as trimethylsilyl (TMS), t-butyldimethylsilyl (TBDMS) tribenzylsilyl, triphenylsilyl, t-butyldiphenylsilyl triisopropyl silyl and the like, substituted ethyl ethers such as 1-ethoxymethyl, 1-methyl-1-methoxyethyl, t-butyl, allyl, benzyl, p-methoxybenzyl, dipehenylmethyl, triphenylmethyl and the like, aralkyl groups such as trityl, and pixyl (9-hydroxy-9-phenylxanthene derivatives, especially the chloride). Ester hydroxy protecting groups include esters such as formate, benzylformate, chloroacetate, methoxyacetate, phenoxyacetate, pivaloate, adamantoate, mesitoate, benzoate and the like. Carbonate hydroxy protecting groups include methyl vinyl, allyl, cinnamyl, benzyl and the like.

BRIEF DESCRIPTION OF THE FIGURES

FIG. 1 depicts plasma concentration against time for male C57B1 mice orally administered a compound of the invention or a compound of the prior art.

DETAILED DESCRIPTION OF THE EMBODIMENTS

Various embodiments of the invention will now be described by way of illustration only with reference to the following Examples and FIG. 1 which depicts plasma concentration against time for male C57B1 mice orally administered a compound of the invention or a compound of the prior art.

Reference Example 1

A P3 Building Block

Step a) 4-Cyanopropiophenone

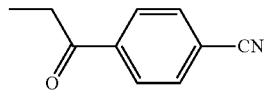

As described for the preparation of 4-cyanoacetophenone (*Synth. Commun* 1994, 887-890), a mixture of 4-bromopropiophenone (5.65 g, 26.4 mmol), $Zn(CN)_2$ (1.80 g, 15.3 mmol), and $Pd(PPh_3)_4$ (2.95 g, 2.6 mmol) was refluxed at 80° C. in deoxygenated DMF (35 mL, stored over 4 Å molecular sieves, bubbled with Ar before use) for 18 h. The mixture was partitioned between toluene (100 mL) and 2N $NH_4OH$ (100 mL). The organic phase was extracted with 2N $NH_4OH$ (100 mL), washed with saturated aqueous NaCl (2×100 mL), dried, and evaporated. A 10 mmol scale reaction was done similarly and the crude products were combined. Flash chromatography (330 g silica, 6/1 petroleum ether—EtOAc) gave white solids (5.17 g, 89%).

1H NMR ($CDCl_3$) δ ppm: 1.22 (t, 3H, J=7.2 Hz), 3.00 (q, 2H, J=7.3 Hz), 7.75 (d, 2H, J=8.8 Hz), 8.03 (d, 2H, J=8.4 Hz)

13C NMR ($CDCl_3$) δ ppm: 7.8, 32.1, 116.1, 117.9, 128.3, 132.4, 139.7, 199.2

Step b) 4-Propionylbenzoic Acid

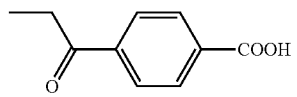

4-Cyanopropiophenone (4.67 g, 29.3 mmol) was refluxed with 2N NaOH (90 mL, 180 mmol) and dioxane (90 mL) at 95° C. overnight. The mixture was diluted with water (150 mL), washed with ether (75 mL), acidified to pH 2 with concentrated HCl, and extracted with ether (3×75 mL). The organic phase was washed with saturated aqueous NaCl (3×75 mL), dried, and evaporated to give yellow solids (5.12 g, 98%).

1H NMR ($CDCl_3+CD_3OD$) δ ppm: 1.18 (t, 3H, J=7.2 Hz), 2.99, (q, 2H, J=7.1 Hz), 7.95 (d, 2H, J=8.4 Hz), 8.08 (d,

Step c) Methyl 4-propionylbenzoate

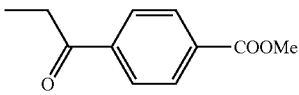

The benzoic acid above (890 mg, 5 mmol), NaHCO3 (1.26 g, 15 mmol) and iodomethane (935 μL, 15 mmol) in DMF (10 mL) were stirred at RT overnight. The mixture was diluted with saturated aqueous NaCl (50 mL) and extracted with ether (3×50 mL). The organic phase was washed with water (50 mL), dried, and evaporated. Flash chromatography (90 g silica, 2/1 petroleum ether—EtOAc) gave white solids (744 mg, 77%).

1H NMR (CDCl$_3$) δ ppm: 1.24 (t, 3H, J=7 Hz), 3.03 (q, 2H, J=7 Hz), 3.95 (s, 3H), 8.0 and 8.12 (ABq, 4H)

Step d) Methyl 4-(2-bromopropionyl)benzoate

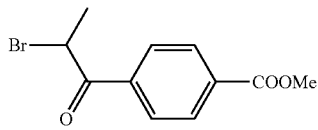

Methyl 4-propionylbenzoate (744 mg, 3.87 mmol), pyrrolidone hydrotribromide (1.98 g), and 2-pyrrolidinone (380 mg, 4.5 mmol) in THF (38 mL) were heated at 50° C. under nitrogen for 3 h. The mixture was cooled, filtered, concentrated, and then redissolved in ether (50 mL). The ether solution was washed successively with water (20 mL), saturated aqueous Na$_2$S$_2$O$_5$ (20 mL), saturated aqueous NaCl (20 mL), and water (20 mL), dried and evaporated to give a yellow oil (1.025 g) that was used directly in the Hantzsch coupling. This material contained 91% of the desired bromoketone, 5% starting ketone, and 4% 4-bromo-1-butanol, as determined by 1H NMR.

1H NMR (CDCl$_3$) δ ppm: 1.92 (d, 3H, J=7 Hz), 3.96 (s, 3H), 5.28 (q, 1 H, J=7 Hz), 8.07 and 8.14 (ABq, 4H)

Step e) 4-[2-(4-tert-Butoxycarbonylpiperazin-1-yl)-5-methylthiazol-4-yl]benzoic Acid Methyl Ester

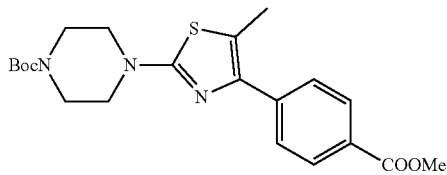 [SMILES: COC(=O)c1ccc(-c2nc(N3CCN(C(=O)OC(C)(C)C)CC3)sc2C)cc1]

All of the α-bromoketone above and 4-thionocarbonylpiperazine-1-carboxylic acid tert-butyl ester (*J. Med. Chem.*, 1998, 5037-5054, 917 mg, 3.73 mmol) were refluxed in 36 mL THF at 70° C. for 2 h, under N$_2$. The precipitate was filtered and the filtrate evaporated to give yellow solids. Flash column chromatography (silica, 5/1 petroleum ether—EtOAc) gave 624 mg of light yellow solids. Chromatography of the precicpitate (silica, 2/1 petroleum ether—EtOAc) gave 32 mg more of compound. Total yield is 44%.

1H NMR (CDCl$_3$) δ ppm: 1.46 (s, 9H), 2.43 (s, 3H), 3.42, (m, 4H), 3.54 (m, 4H), 3.90 (s, 3H), 7.68 and 8.04 (ABq, 4H).

Step f) 4-[2-(4-tert-Butoxycarbonylpiperazin-1-yl)-5-methylthiazol-4-yl]benzoic Acid

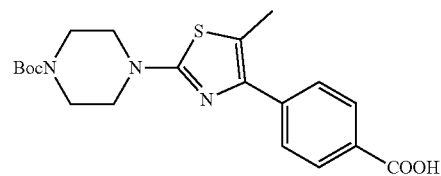 [SMILES: Cc1sc(N2CCN(C(=O)OC(C)(C)C)CC2)nc1-c1ccc(C(=O)O)cc1]

The above methyl ester (564 mg, 1.35 mmol) was heated with 1.35 mL 2 N NaOH, 5 mL THF, and 3.65 mL water at 60° C. for 4 h. The reaction mixture was evaporated, poured into 20 mL saturated aqueous NaCl and 20 mL CH2012, and then acidified to pH 3 with 5% citric acid, in an ice bath. The layers were separated and the organic phase was extracted further with 2×10 mL CH$_2$Cl$_2$. The organic phases were combined, washed with water (10 mL), dried, and evaporated to give light yellow solids (537 mg, 98%).

1H NMR (CDCl$_3$) δ ppm: 1.48 (s, 9H), 2.47 (s, 3H), 3.47 (m, 4H), 3.57 (m, 4H), 7.74 and 8.12 (ABq, 4H).

$^{13}$C NMR (CDCl$_3$) δ ppm: 12.6, 28.3, 42.8, 48.1, 80.3, 119.1, 127.8, 128.2, 130.1, 140.5, 145.6, 154.6, 167.2, 171.4.

LCMS: (M+H)$^+$ 404, (M−H)$^-$ 402.

Step g) 4-[5-methyl-2-(4-methyl-piperazin-1-yl)-thiazol-4-yl]benzoic Acid

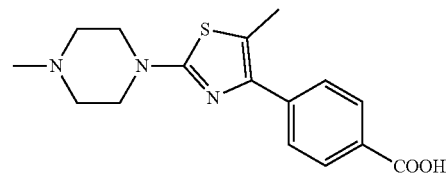 [SMILES: Cc1sc(N2CCN(C)CC2)nc1-c1ccc(C(=O)O)cc1]

4-[4-(4-Carboxy-phenyl)-5-methyl-thiazol-2-yl]-piperazine-1-carboxylic acid tert-butyl ester (0.421 mmol) was dissolved in 4M HCl in 1,4-dioxane, and stirred at room temperature for 1 h. The solvent was then removed under vacuum, and the residue 4-(5-methyl-2-piperazin-1-yl-thiazol-4-yl)-benzoic acid was suspended in methanol (10 ml) and treated with AcOH/AcONa buffer (pH ~5.5, 5 ml), and formaldehyde (0.547 mmol). The reaction mixture was stirred at room temperature for 1 h, then treated with NaCNBH$_3$ (0.547 mmol) and stirred at room temperature overnight. The solvent was then removed under vacuum, and the residue was purified by column chromatography to afford the title compound (0.403 mmol, 95%).

MS(ES) m/z 318 (100%, [M+H]$^+$).

Reference Example 2

An Alternative P3 Building Block

3-Fluoro-4-[2-(4-methylpiperazin-1-yl)-thiazol-4-yl]benzoic Acid HCl Salt

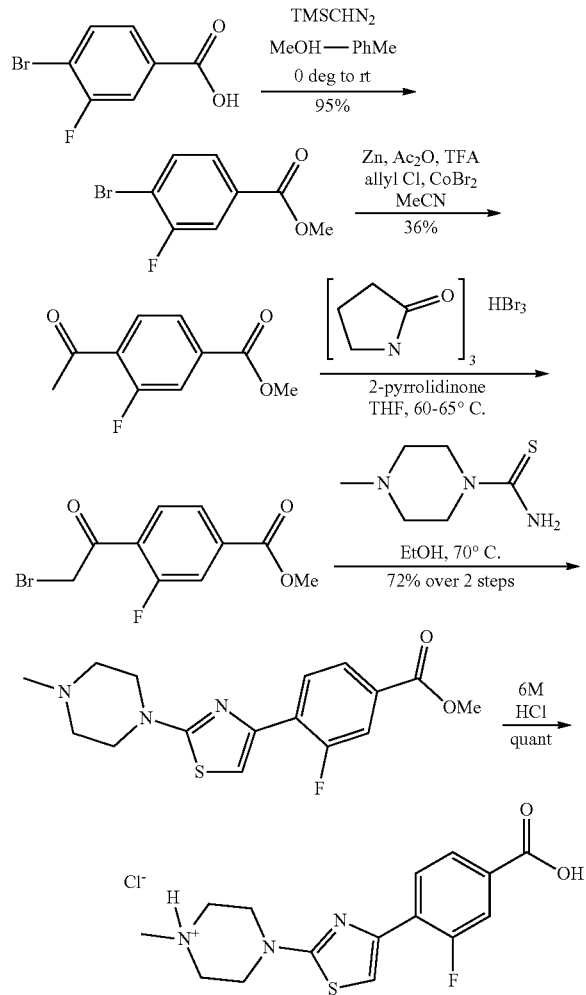

Step a) Methyl 4-bromo-3-fluorobenzoate

4-Bromo-3-fluorobenzoic acid (2.46 g, 11.2 mmol) was dissolved in MeOH (9 mL) and toluene (4 mL) and cooled in an ice bath. (Trimethylsilyl)diazomethane (11 mL, 2.0 M in hexanes, 22 mmol) was added dropwise until the yellow color persisted. The solution was stirred at room temperature for 40 mins and then concentrated in vacuo. A second batch of carboxylic acid (2.43 g) was treated similarly. The crude product from both batches were combined and subjected to flash chromatography (silica, 5/1 pentane—EtOAc) to give the methyl ester as white solids (4.92 g, 95% yield).

$^1$H NMR (400 MHz, CDCl$_3$) delta ppm 7.77 (m, 1 H), 7.71 (m, 1 H), 7.64 (m, 1 H), 3.93 (s, 3H).

Step b) Methyl 4-acetoxy-3-fluorobenzoate

Allyl chloride (105 μL, 1.28 mmol) and TFA (20 μL, 0.26 mmol) were added to a suspension of zinc dust (480 mg, 7.34 mmol) and anhydrous cobalt(II) bromide (96.6 mg, 0.44 mmol) in MeCN (4 mL), under inert gas. After stirring at room temperature for 10 min, the aryl bromide (1.003 g, 4.30 mmol dissolved in 5 mL MeCN) from (a) was added, followed by acetic anhydride (0.45 mL, 4.79 mmol) and more MeCN (1 mL). The mixture was stirred overnight, quenched with 1M HCl (20 mL), and then extracted with EtOAc (3×20 mL). The organic phase was washed successively with saturated aqueous NaHCO$_3$ (20 mL) and saturated NaCl (2×20 mL), dried (Na$_2$SO$_4$), and concentrated. Flash chromatography (silica, 6/1 to 4/1 petroleum ether—EtOAc gave recovered bromide (161.1 mg, 16%) and the desired ketone (white solids, 305.5 mg, 36%).

NMR (CDCl$_3$) δ ppm: $^1$H (400 MHz) 7.94-7.86 (m, 2H), 7.80 (dd, 1 H, J=11.2, 1.6 Hz), 3.95 (s, 3H), 2.67 (d, 3H, J=4.4 Hz); $^{19}$F (376 MHz) -109.2 (m); $^{13}$0 (100 MHz) 195.4 (d, J=3.7 Hz), 165.1 (d, J=2.2 Hz), 161.6 (d, J=255 Hz), 135.8 (d, J=8.1 Hz), 130.7 (d, J=2.9 Hz), 129.0 (d, J=14 Hz), 125.2 (d, J=3.6 Hz), 117.9 (d, J=26 Hz), 52.7 (s), 31.4 (d, J=7.3 Hz).

Step c) Methyl 4-(2-bromoacetoxy)-3-fluorobenzoate

THF (10 mL) and 2-pyrrolidinone (91 μL, 1.20 mmol) were added to a mixture of the ketone from b) (198 mg, 1.01 mmol) and pyrrolidone hydrotribromide (532 mg, 1.07 mmol). After heating at 60-65° C. for 2 h, the mixture was concentrated under vacuum and then partitioned between EtOAc (20 mL) and saturated Na$_2$S$_2$O$_3$ (10 mL). The aqueous phase was extracted with EtOAc (10 mL). The organic phases were combined, washed with saturated NaCl (2×10 mL), dried (Na$_2$SO$_4$), and concentrated. Flash chromatography (silica, 7/1 petroleum ether—EtOAc) gave white solids (0.2634 g) containing 84% of the desired bromide (as determined by integration of $^{19}$F NMR peaks).

NMR (CDCl$_3$) δ ppm: $^1$H (400 MHz) 7.93 (m, 1H), 7.88 (m, 1H), 7.79 (dd, 1H, J=11.2, 1.6 Hz), 4.50 (d, 2H, J=2.4 Hz), 3.94 (s, 3H); $^{19}$F (376 MHz) -108.4 (m).

Step d) Methyl 3-fluoro-4-[2-(4-methylpiperazin-1-yl)-thiazol-4-yl]benzoate

EtOH (5.0 mL) was added to the bromoketone above (193 mg, 0.70 mmol) and 4-methyl-piperazine-1-carbothioic acid amide (113 mg, 0.71 mmol) and the mixture was heated at 70° C. for 2h 15 min. The precipitates were filtered, washed with cold EtOH, and dried under vacuum and characterized. The procedure was repeated in a larger scale for 1.75 g bromoketone (6.36 mmol).

NMR (1/1 CDCl$_3$-CD$_3$OD) δ ppm: $^1$H (400 MHz) 8.20 (m, 1H), 7.86 (dd, 1H, J=8.4, 1.6 Hz), 7.76 (dd, 1 H, J=11.4, 1.8 Hz), 7.38 (d, 1 H, J=2.4 Hz), 4.23 (br, 2H), 3.95, (s, 3H), 3.65 (br, 4H), 3.32 (br, 2H), 2.98 (s, 3H); $^{19}$F (376 MHz) -114.0 (m). LCMS [M+H]$^+$=336.

The precipitates from both preparations were combined and suspended in saturated NaHCO$_3$ (50 mL). The mixture was extracted with EtOAc. The organic phase was washed with water, dried (Na$_2$SO$_4$), and evaporated to give the title compound as cream solids (1.76 g).

Step e) 3-fluoro-4-[2-(4-methylpiperazin-1-yl)-thiazol-4-yl]benzoic acid HCl salt The methyl ester (1.76 g, 5.25 mmol) from (d) was heated at 80° C. with 6M HCl (40 mL) for 5.5 h. More 6M HCl (10 mL) was added and the mixture was heated at 90° C. for 1 h 15 min. After cooling, the mixture was then evaporated under vacuum and freeze-dried from water to give the final product as cream solids in quantitative yield.

NMR (DMSO-d6) δ ppm: $^1$H (400 MHz) 11.60 (br, 1H), 8.18 (t, 1H, J=8.0 Hz), 7.82 (dd, 1H, J=8.4, 1.6 Hz), 7.72 (dd, 1H, J=12.0, 1.6 Hz), 7.48 (d, 1H, J=2.8 Hz), 4.11 (m, 2H), 3.58 (m, 2H), 3.49 (m, 2H), 3.19 (m, 2H), 2.80 (d, 3H, J=4.4 Hz); $^{19}$F (376 MHz) -113.5 (m); $^{13}$C (100 MHz) 168.9, 166.0, 159.0 (d, J=250 Hz), 143.4, 131.4 (d, J=8 Hz), 129.8, 125.8 (d, J=11 Hz), 125.6, 116.6 (d, J=24 Hz), 111.1 (J=15 Hz), 51.1, 45.0, 41.9. LCMS [M+H]$^+$=322.

Reference Example 3

6-aldehyde-intermediate

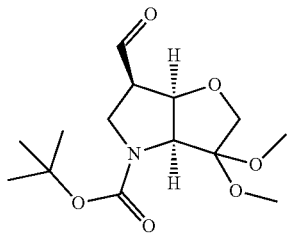 [SMILES: COC1(OC)CO[C@@H]2[C@H](C=O)CN(C(=O)OC(C)(C)C)[C@@H]21]

6-Formyl-3,3-dimethoxy-hexahydro-furo[3,2-b]pyrrole-4-carboxylic Acid Tert-Butyl Ester Step a

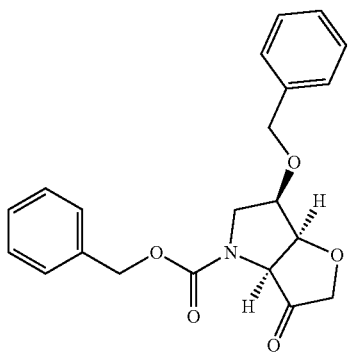 [SMILES: O=C1CO[C@H]2[C@@H]1N(C(=O)OCc1ccccc1)C[C@H]2OCc1ccccc1]

(3as, 6aS)-6R-benzyloxy-3-oxo-hexahydro-furo[3,2-b]pyrrole-4-carboxylic Acid Benzyl Ester (1a)

Dess-Martin reagent (12.5 g, 30 mmol) was dissolved in DCM (250 mL). 6-Benzyloxy-3-hydroxy-hexahydro-furo[3,2-b]pyrrole-4-carboxylic acid benzyl ester (prepared as described in WO05/066180) (7.4 g, 20 mmol) in DCM (50 mL) was added to a stirred solution of oxidant at rt under a nitrogen atmosphere over 45 min. After an additional 90 min stirring the reaction was deemed to be complete by TLC. Aqueous 10% Na$_2$S$_2$O$_3$ (200 mL) was added and the mixture was stirred at rt for another 15 minutes. The two phase system was transferred into a separation funnel and extracted twice with EtOAc (200 mL and 100 mL respectively). The combined organic phases were washed once with aqueous saturated NaHCO$_3$ (100 mL) and brine (100 mL), dried over Na$_2$SO$_4$, filtered and the solvent removed in vacuo, yielding the crude product title compound as a clear oil (7.69 g,); ESI+, m/z: 368 (M++1).

Step b

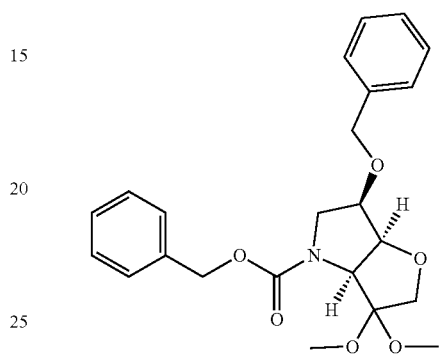

(3aS,6aS)-6R-benzyloxy-3,3-dimethoxy-hexahydro-furo[3,2-b]pyrrole-4-carboxylic Acid Benzyl Ester (1b)

The keto derivative (1a) (7.6 g) was dissolved in dry methanol (100 mL). Trimethyl orthoformate (30 mL) and pTsOH (0.2 g) was added at rt under a nitrogen atmosphere. The mixture was heated at 60° C. for 8 hours. When the reaction was deemed to have reached completion according to TLC, it was cooled to rt and concentrated in vacuo. The crude product was purified by column chromatography over silica gel eluting with ethyl acetate-heptane (1:4) which gave the title compound as a clear oil (5.9 g, 71% over 2 steps); ESI+, m/z: 382 (M+−OMe).

Step c

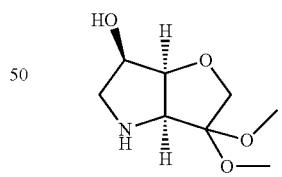

(3aS,6aS)-3,3-dimethoxy-hexahydro-furo[3,2-b]pyrrol-6R-ol (1c)

A solution of compound (1b) (2.5 g, 6.4 mmol) in methanol (60 mL) and Pd(OH)$_2$ (0.7 g) was stirred at rt under H2 atmosphere for 48 hours. When the reaction was deemed to have reached completion according to TLC, the mixture was filtered and concentrated in vacuo to yield the crude title compound as a brownish oil (1.15 g); ESI+, m/z: 190 (M++1).

Step d

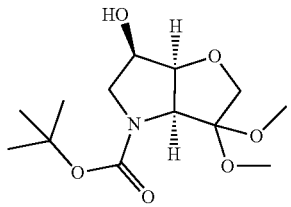 [SMILES: COC1(OC)CO[C@@H]2[C@H](O)CN(C(=O)OC(C)(C)C)[C@@H]21]

(3aS, 6aS)-6R-hydroxy-3,3-dimethoxy-hexahydro-furo[3,2-b]pyrrole-4-carboxylic Acid Tert-Butyl Ester (1d)

3,3-Dimethoxy-hexahydro-furo[3,2-b] pyrrol-6-ol (1c) (2.80 g, 14.8 mmol) was dissolved in 75 mL of a mixture of dioxan/water (2:1). A solution of 10% $Na_2CO_3$ (25 mL) was added drop wise to pH 9-9.5. The mixture was cooled to 0° C. in an ice-water bath and Boc anhydride was added in one portion. The reaction was stirred at rt overnight and the pH of the mixture was maintained at 9-9.5 by addition of more 10% solution of $Na_2CO_3$ if necessary. The reaction was monitored by TLC (50:50 ethyl acetate:isohexane). Once completed, the mixture was filtered to eliminate the salts formed and the solvent was evaporated in vacuo. The aqueous mixture was extracted with 3×100 mL EtOAc, the combined organic phases were washed with 100 mL of water and 100 mL brine, dried over $Na_2SO_4$, filtered and the solvent was evaporated in vacuo to afford 3.79 g of the title carbamate as a clear oil (89%), 94% pure (HPLC), $ESI^+$, m/z: 312 (M++Na).

Step e

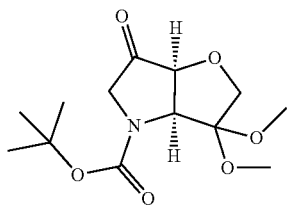 [SMILES: COC1(OC)CO[C@@H]2C(=O)CN(C(=O)OC(C)(C)C)[C@@H]21]

3,3-Dimethoxy-6-oxo-hexahydro-furo[3,2-b]pyrrole-4-carboxylic Acid Tert-Butyl Ester (1e)

To the alcohol (1e) (3.674 g, 12.70 mmol) dissolved in DCM (80 mL) was added Dess-Martin Periodinane (7.00 g, 16.5 mmol) and the solution was stirred for 3 h at room temperature. The reaction was then quenched by the addition of 10% $Na_2S_2O_3$ (aq) (150 mL) and the resulting slurry was stirred for 15 minutes. The mixture was transferred to a separation funnel and the phases were separated. The aqueous phase was extracted trice with DCM and the combined organic phases were subsequently washed twice with sat. $NaHCO_3$ solution and were the dried, filtered, and concentrated. The crude material was purified by flash column chromatography (toluene/ethyl acetate 3:1) which gave the title compound (2.882 g, 79%).

Step f

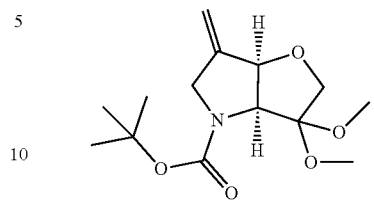

3,3-Dimethoxy-6-methylene-hexahydro-furo[3,2-b]pyrrole-4-carboxylic Acid Tert-Butyl Ester (1f)

The keto compound 1e (1.10 g, 3.83 mmol) was dissolved in dry THF (30 mL) and the solution was cooled to 0° C. A solution of methyl triphenylphosphonium bromide (4.0 g, 11.2 mmol) and KOtBu (1.17 g, 10.5 mmol) in dry THF (40 mL) was added in 3 aliquots with 2 hours interval. After 6 hrs the solution was poured into a separatory funnel with diethyl ether (70 mL) and extracted with 10% citric acid $(a_q)$(2*40 mL). The organic phase was washed with saturated aqueous $NaHCO_3$ (40 mL), dried with $Na_2SO_4$, filtered and the solvent was evaporated in vacuo. The crude product was purified by flash chromatography (heptane:ethyl acetate 4:1) which gave the title compound (524 mg, 48%)

[1] H NMR ($CDCl_3$, 400 MHz) δ 1.48 (s, 9H), 3.27 (s, 3H), 3.40 (d, 3H, J=16.6), 3.57-3.64 (m, 1H), 3.84 (d, 1H, J=9.5), 3.92 (d, 1H, J=16.3), 4.07-4.25 (m, 1H), 4.35-4.49 (m, 1H), 4.98 (bs, 1H), 5.22 (d, 1H, J=16.4), 5.34 (s, 1H).

Step g

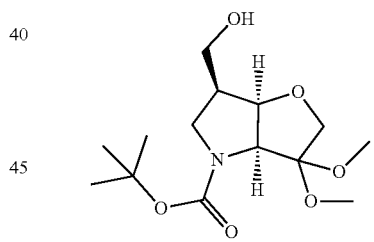

6-Hydroxymethyl-3,3-dimethoxy-hexahydro-furo[3,2-b]pyrrole-4-carboxylic Acid Tert-Butyl Ester (1g)

The olefin 1e (524 mg, 1.84 mmol) was dissolved in dry THF (70 mL). 9-BBN-H (0.5 M in THF) (7.34 mL, 3.67 mmol) was added and the solution was stirred over night. The solvent was removed by rotary evaporation and redissolved in THF (20 mL). MeOH (10 mL) was slowly added to the solution and when the gas evolution had ceased, $H_2O$ (20 mL) was added to the solution followed by $NaBO_3$. The solution was filtered after it had been stirred for 18 hrs and the filtrate was diluted with EtOAc (70 mL) and washed with brine (2*50 mL). The organic phase was dried with $Na_2SO_4$, filtered and the solvent was evaporated in vacuo. The crude product was purified by flash chromatography (heptane: ethyl acetate 2:1) which gave the title compound (477 mg, 86%).

¹H NMR (CDCl₃, 400 MHz) δ1.47 (s, 9H), 2.09-2.25 (m, 2H), 3.02-3.20 (m, 1 H), 3.29 (s, 3H), 3.39 (s, 3H), 3.65-3.93 (m, 4H), 4.44 (d, 1 H, J=5.7), 4.70-4.84 (m, 1 H).

Step h

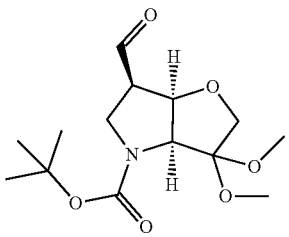 [SMILES: COC1(OC)CO[C@@H]2[C@H](C=O)CN(C(=O)OC(C)(C)C)[C@@H]21]

6-Formyl-3,3-dimethoxy-hexahydro-furo[3,2-b]pyrrole-4-carboxylic Acid Tert-Butyl Ester (1h)

To a solution of the alcohol 1 g (370 mg, 1.22 mmol) dissolved in dry DCM (10 mL) was added Dess Martin periodinane (673 mg, 1.59 mmol). The reaction was stirred for 40 minutes and then quenched by addition of 10 mL of 10% Na₂S₂O₃:NaHCO₃₍sat₎ 1:1. The solution was diluted with DCM (50 mL) and extracted with a 1:1 mixture of 10% Na₂S₂O₃:NaHCO₃₍sat₎ (50 mL). The organic phase was dried with Na₂SO₄, filtered and evaporated. The crude product was purified by flash chromatography (heptane: ethyl acetate (2:1) which gave the title compound (290 mg, 79%)).

¹H NMR (CDCl₃, 400 MHz) δ1.47 (s, 9H), 2.90-3.06 (m, 1 H), 3.29 (s, 3H), 3.38 (s, 3H), 3.67-3.85 (m, 2H), 3.88-4.55 (m, 3H), 4.93-5.19 (m, 1 H), 9.64* and 9.80* (s, 1H). * Two peaks due to rotamers.

Reference Example 4

6-acetylene P1 Building Block

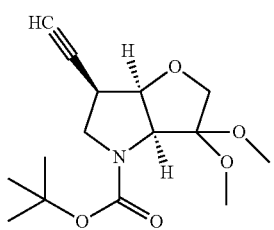 [SMILES: C#C[C@@H]1CN(C(=O)OC(C)(C)C)[C@H]2[C@@H]1OCC2(OC)OC]

6-Ethynyl-3,3-dimethoxy-hexahydro-furo(3,2-b) pyrrole-4-carboxylic Acid Tert Butyl Ester Step a)

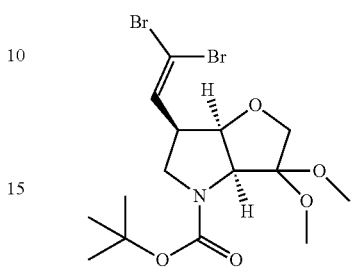

The aldehyde of Reference Example 3 (318.3 mg, 1.06 mmol) in 6 mL dichloromethane (DCM) was added dropwise to a solution of CBr4 (700 mg, 2.11 mmol) and PPh₃ (1.10 g, 4.19 mmol) in 10 mL DCM, with cooling in an ice bath. After stirring at 0° C. for 2 h, the mixture was diluted with 30 mL iso-hexane and then filtered through a short Celite column. The column was washed with 20 mL i-hexane, followed by 3/1 i-hexane—DCM. The filtrate was evaporated to give light yellow solids. Flash chromatography (silica, 3/1 i-hexane—EtOAc) gave compound 2 (339.5 mg, 70% yield).

1H NMR (400 MHz, CDCl₃) δ 6.55 (d, 1 H, J=8.8 Hz, HC=CBr2), 4.64 (br s, 1 H), 4.42 (d, 1 H, J=5.2 Hz), 4.10-3.90 (br m, 1 H), 3.85-3.65 (m, 2H), 3.37 (s, 3H, OMe), 3.29 (s, 3H, OMe), 3.00 (m, 1 H), 2.84 (br s, 1 H).

Step b)

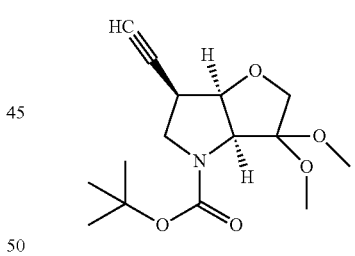

Butyllithium solution (1.6M in hexanes, 1.50 mL) was added dropwise at -78° C. to a solution of the dibromoalkene of step a (327.5 mg, 0.72 mmol) in 13 mL THF. After stirring at -78° C. for 1.75 h, the reaction was quenched with 3 mL saturated aqueous NH₄Cl. The reaction mixture was concentrated, then partitioned between 30 mL saturated aqueous NaCl and 30 mL EtOAc. The aqueous phase was extracted with 2×30 mL EtOAc. The organic phases were combined, dried (Na₂SO₄), and evaporated to give a yellow oil. Flash chromatography (silica, 3/1 i-hexane—EtOAc) gave title compound as white solids (161.7 mg, 67% yield).

1H NMR (500 MHz, CDCl₃) δ 4.67 (br s, 1 H), 4.40 (br s, 1 H), 4.16-4.0 (br m, 1 H), 3.88-3.74 (m, 2H), 3.37 (s, 3H, OMe), 3.29 (s, 3H, OMe), 3.16 (br s, 1H), 2.81 (br s, 1H, HC—C≡CH), 2.20 (d, 1 H, C≡CH), 1.47 (s, 9H, tBu).

Reference Example 5

A Typical P1/P2 Coupling & Deprotection

Step a)

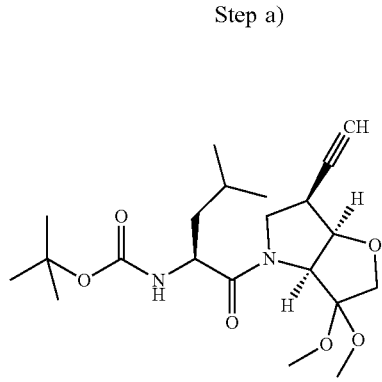

Acetyl chloride (0.51 mL) was added dropwise to a solution of the terminal alkyne of Reference Example 4 (153 mg, 0.514 mmol) in MeOH (4.6 mL), chilled in an ice bath. The reaction mixture was stirred at RT overnight and then evaporated. Boc-Leu-OH—H$_2$O (145 mg, 0.58 mmol) was added and the mixture was coevaporated from DMF, then redissolved in 5 mL DMF, and cooled in an ice bath. DIEA (0.36 mL, 2.1 mmol) was added, followed by HATU (220 mg, 0.578 mmol). After stirring at 0° C. for 15 min, the mixture was stirred at RT for 3 h and then concentrated. The mixture was dissolved in 20 mL EtOAc, washed successively with saturated aqueous NaHCO$_3$ (10 mL) and saturated aqueous NaCl (2×10 mL), dried (Na$_2$SO$_4$), and evaporated to give a yellow-brown oil. Flash chromatography (silica, 1/1 i-hexane—EtOAc) gave title compound (213 mg, quantitative).

HPLC-MS: single peak, mass 411 [M+H]$^+$, R$_t$=3.15 min (gradient 5 to 99% B in 3 min, then 100% B for 1.5 min)

Method—Flow: 0.8 mL/min, UV=210-400 nm, ACE C8 3×50 mm; Mobile phase A: 10 mM NH$_4$Ac in 90% H$_2$O, B: 10 mM NH$_4$Ac in 90% MeCN Step b)

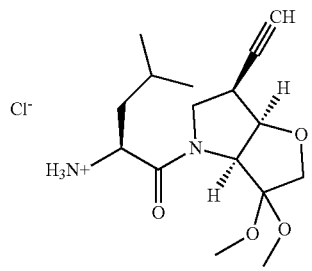 [SMILES: [Cl-] ; C#C[C@@H]1CN(C(=O)[C@@H]([NH3+])CC(C)C)[C@H]2[C@@H]1OCC2(OC)OC]

Boc deprotection of the compound of step a) (0.514 mmol) was done as for Reference Example 4 above to give the title HCl salt. The salt was dissolved in CH$_2$Cl$_2$ and divided into three portions, evaporated separately to give 0.17 mmol per sample.

Reference Example 6

An Alternative P3 Building Block

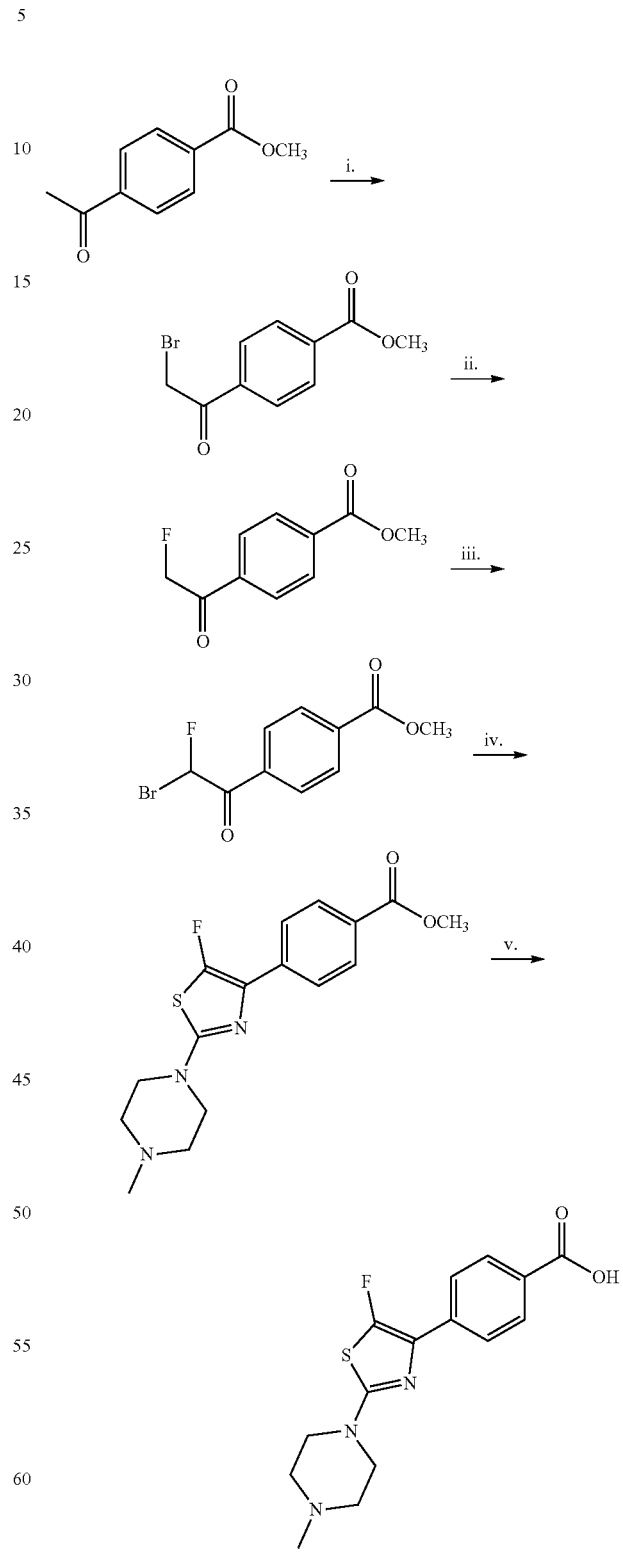

i. AcOH, bromine, RT, 2 h, 55% yield; ii. KF, acetonitrile, 18-crown-6, 90° C., 16 h; 31 yield; iii. AcOH, bromine, 45° C., 4 h, 100% yield; iv. 4-Methyl-piperazine-1-carbothioic acid amide, Δ, 2 h, 74% yield; LiOH, RT, 16 h, 100% yield.

Availability of Starting Materials

Methyl 4-acetylbenzoate is available from Aldrich; 4-methyl-piperazine-1-carbothioic acid amide—11 suppliers found in SciFinder (perhaps Chem Pur Products Ltd in Germany most convenient).

Step a) 4-(2-Bromo-acetyl)-benzoic Acid Methyl Ester

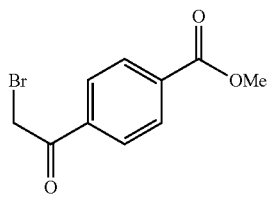 [SMILES: COC(=O)c1ccc(C(=O)CBr)cc1]

To a solution of 4-acetyl-benzoic acid methyl ester (8.4 mmol) in acetic acid (20 mL) was added bromine (8.4 mmol). The reaction was stirred at RT for 2 h over which time the red colour disappeared and an off white precipitate formed. The product was collected by filtration and washed with cold methanol/water (200 mL 1:1) to yield a white powder (55%). 1H NMR (400 MHz, CDCl$_3$) 3.98 (3H, s), 4.20 (2H, s), 8.02 (2H, d, J=8Hz), 8.18 (2H, d, J=8Hz).

Step b) 4-(2-Fluoro-acetyl)-benzoic Acid Methyl Ester

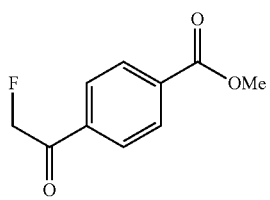 [SMILES: COC(=O)c1ccc(C(=O)CF)cc1]

To a suspension of potassium fluoride (3.11 mmol) in acetonitrile (1 mL) was added 18-crown-6 (0.1 mmol) and the reaction was heated at 90° C. for 30 mins. 4-(2-Bromo-acetyl)-benzoic acid (1.56 mmol) was added and the reaction heated at 90° C. for 16 h. The reaction was diluted with water (10 mL) and extracted with ethyl acetate (3×20 mL). The product was purified on silica eluting with 5-15% ethyl acetate in iso-hexane to yield on concentration in vacuo of the desired fractions, the title product as a white solid (31%). 1H NMR (400 MHz, CDCl$_3$) 3.98 (3H, s), 5.55 (2H, d, J=50Hz), 7.95 (2H, d, J=8Hz), 8.18 (2H, d, J=8Hz).

Step c) 4-(2-Bromo-2-fluoro-acetyl)-benzoic Acid Methyl Ester

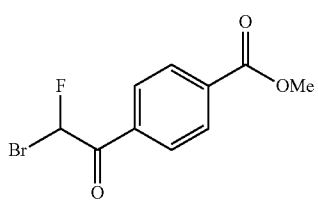 [SMILES: COC(=O)c1ccc(C(=O)C(F)Br)cc1]

To a suspension of 4-(2-fluoro-acetyl)-benzoic acid (1.19 mmol) in acetic acid (5 mL) was added bromine (1.19 mmol). The reaction was heated at 45° C. for 4 h over which time a green solution formed. The reaction was concentrated in vacuo and azeotroped twice with toluene to yield the title compound as a green solid (100%). The product was used crude in the next step. 1H NMR (400 MHz, CDCl$_3$) 3.98 (3H, s), 7.04 (1H, s), 8.05 -8.10 (4H, m).

Step d) 4-[5-Fluoro-2-(4-methyl-piperazin-1-yl)-thiazol-4-yl]-benzoic Acid Methyl Ester

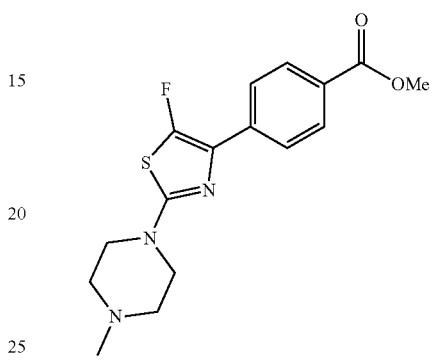

4-(2-Bromo-2-fluoro-acetyl)-benzoic acid methyl ester (1.18 mmol) and 4-methyl-piperazine-1-carbothioic acid amide (1.18 mmol) were dissolved in ethanol (10 mL). The reaction was heated at reflux for 2 h. The reaction was cooled to RT causing the product to precipitate. The product was collected by filtration and washed with cold ethanol. The product was given an aqueous sodium bicarbonate work up to yield the title compound as a colourless oil (74%). MS (ES+) 337 (M+H, 100%).

Step f)

4-[5-Fluoro-2-(4-methyl-piperazin-1-yl)-thiazol-4-yl]-benzoic Acid Di-Hydrochloride

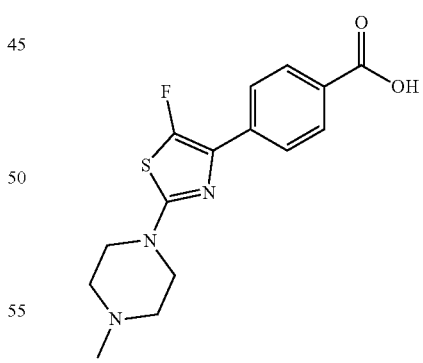

To a solution of 4-[5-fluoro-2-(4-methyl-piperazin-1-yl)-thiazol-4-yl]-benzoic acid methyl ester (0.43 mmol) in tetrahydrofuran/water (2.5 mL, 4:1) was added lithium hydroxide (0.5 mmol). The reaction was stirred at RT for 16 h. The reaction was concentrated in vacuo and hydrochloric acid (2N, 3 mL) was added causing the product to precipitate as a white solid. The product was collected by filtration to yield the title product as a white solid (79%). MS (ES+) 322 (M+H, 100%).

Reference Example 7

An Alternative P1 Building Block

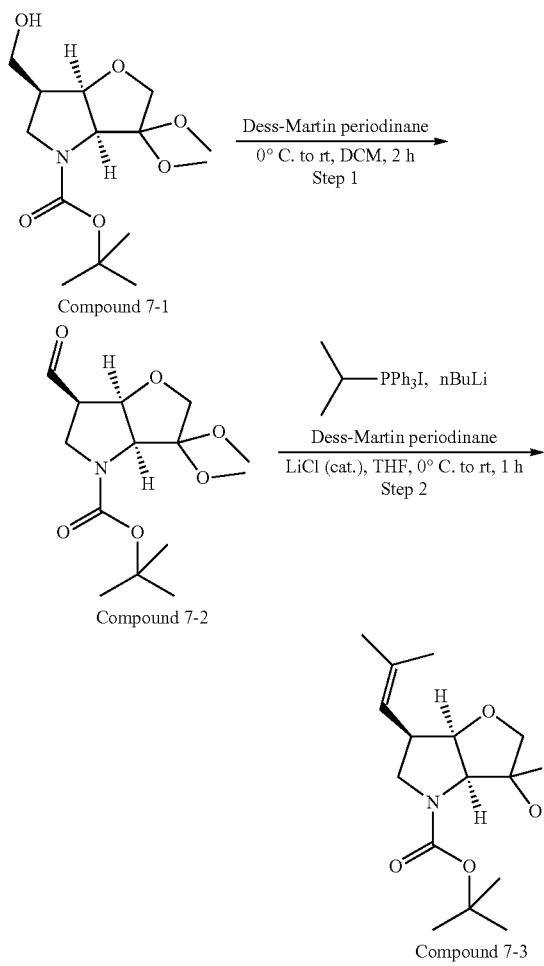

Step a) Oxidation of Alcohol 7-1

A solution of compound 7-1 (0.85 g, 2.8 mmol) (see reference example 3 step g) in dry $CH_2Cl_2$ (15 mL) was purged with argon for 30 minutes. Dess-Martin periodinone (1.78 g, 4.2 mmol) was added at 0° C. and the reaction mixture was stirred at room temperature for 2 hours. When the reaction was deemed to have reached completion, the reaction was quenched with 10% $Na_2S_2O_3$ solution. The reaction mixture was diluted with $CH_2Cl_2$ (30 mL), and then washed in turn with saturated $Na_2S_2O_3$ solution (2×50 mL), and saturated sodium bicarbonate solution (2×50 mL). The organic layer was then dried over anhydrous sodium sulfate, filtered and the filtrate conc in vacuo at room temperature. The crude product aldehyde 7-2 (0.75 g, crude) was used in the next step without further purification.

TLC: EtOAc: Pet ether 1:1 $R_f$=0.5.

Step b) Wittig Reaction With Compound 7-2

To a stirred solution of isopropyltriphenylphosphonium iodide (6.48 g, 0.015 mol) (co-evoparated with dry toluene prior to start of the reaction) in dry THF (20 mL) was added a solution of n-BuLi (10.7 mL, 0.0172 mol, 1.6 M in hexane) at −10° C. under nitrogen atmosphere and further stirred at 0° C. for 1 hour. The color of the reaction mixture slowly turned to dark orange color. A solution of compound 2 (0.75 g, 0.0025 mol) and anhydrous lithium chloride (~1.5 mg) in dry THF (20 mL) was slowly added to the reaction mixture at 0° C. under a nitrogen atmosphere. The reaction mixture was further stirred for 30 minutes maintaining the same temperature and then slowly warmed to rt and stirred for another 30 minutes. The reaction mixture was then quenched with saturated ammonium chloride solution (20 mL). The crude product was extracted with EtOAc (2×30mL) and the organic layer was washed with brine (50 mL), and dried over anhydrous sodium sulfate. The solvent was removed in vacuo and the crude product was purified by column chromatography (neutral alumina, eluent 1% EtOAc in pet ether) to afford pure compound 7.3 (0.19 g, yield 21% over two steps).

Reference Example 8

An Alternative P1-P2 Building Block

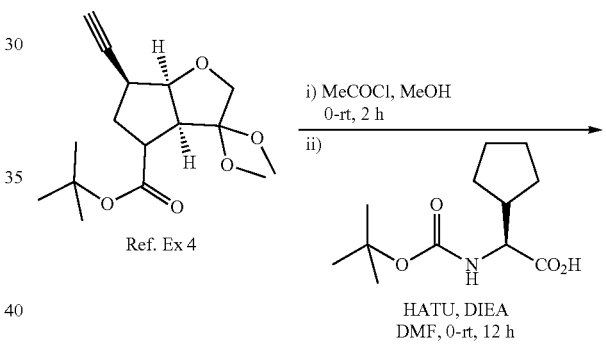

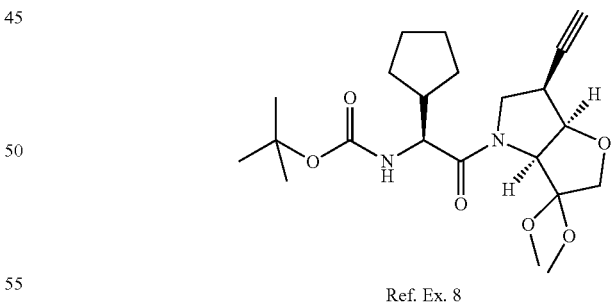

Ref. Ex. 8

The initial reaction was carried out in a similar way as reported for reference example 5 but instead using 4 (0.2 g, 0.67 mmol) in dry MeOH (15 mL) and acetyl chloride (0.66 mL) to get the Boc-deprotected amine compound which was then treated with Boc-cyclopentyl glycine (0.17 g, 0.7 mmol), HATU (0.27 g, 0.7 mmol) and DIEA (0.45 mL,. 2.6 mmol) in dry DMF (7 mL) to get the pure title compound [0.195 g, yield 68%].

TLC system: EtOAc: pet ether 1:1 v/v, $R_f$=0.4

Reference Example 9

Probe Compound for the Feasibility of Dihalovinyl P1

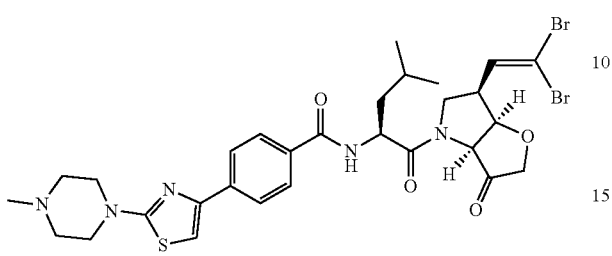

This compound tests the synthetic and biological feasibility of a dihalovinyl P1 end product. It will be appreciated that introduction of 6-difluorovinyl by the corresponding Wittig reaction of reference example 3 is trivial and that preparation of a biologically active end-product provides confidence that the claimed difluorvinyl compounds are also synthetically stable and active.

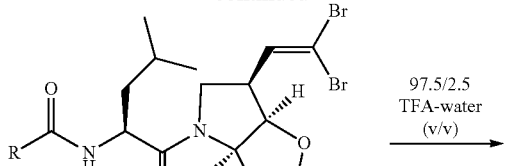

9-4

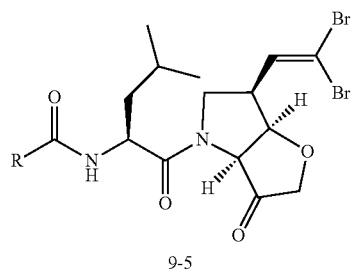

9-5

Step a)

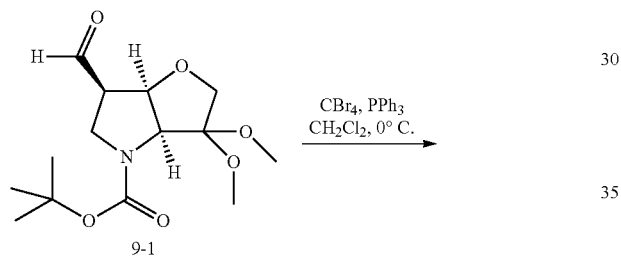

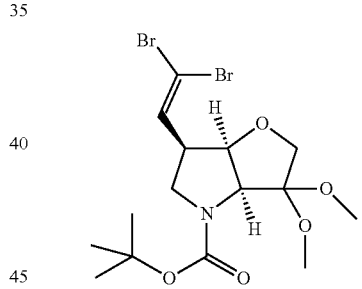

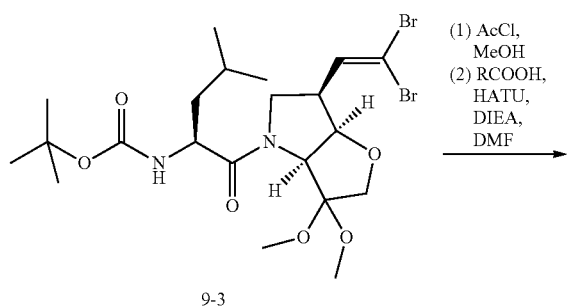

The aldehyde 9-1 (318.3 mg, 1.06 mmol) (see reference example 3) in 6 mL dichloromethane (DCM) was added dropwise to a solution of $CBr_4$ (700 mg, 2.11 mmol) and $Ph_3P$ (1.10 g, 4.19 mmol) in 10 mL DCM, with cooling in an ice bath. After stirring at 0° C. for 2 h, the mixture was diluted with 30 mL iso-hexane and then filtered through a short Celite column. The column was washed with 20 mL i-hexane, followed by 3/1 i-hexane—DCM. The filtrate was concentrated in vacuo to give light yellow solids. Flash chromatography (silica, 3/1 i-hexane—EtOAc) gave compound 9-2 (339.5 mg, 70% yield).

1H NMR (400 MHz, $CDCl_3$) δ 6.55 (d, 1 H, J=8.8 Hz, $\underline{H}C=CBr_2$), 4.64 (br s, 1 H), 4.42 (d, 1 H, J=5.2 Hz), 4.10-3.90 (br m, 1 H), 3.85-3.65 (m, 2H), 3.37 (s, 3H, O$\underline{Me}$), 3.29 (s, 3H, O$\underline{Me}$), 3.00 (m, 1 H), 2.84 (br s, 1 H).

Rf (TLC 1/1 isohexane—EtOAc) 0.79.

HPLC-MS: ion cluster $[M+Na]^+$ 478 (8%), 480 (15%), 482 (7%), $R_t$=3.56 min (gradient 5 to 99% B in 3 min, then 100% B for 1.5 min)

Step b)

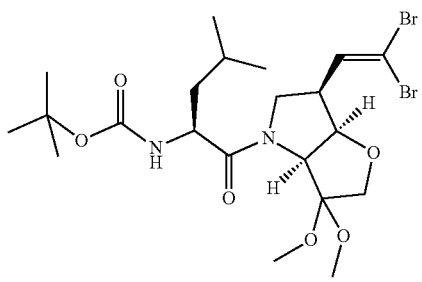 [SMILES: COC1(OC)CO[C@@H]2[C@H](C=C(Br)Br)CN(C(=O)[C@H](CC(C)C)NC(=O)OC(C)(C)C)[C@@H]21]

Acetyl chloride (0.18 mL) was added dropwise to a solution of the dibromoalkene 9-2 (81.7 mg, 0.179 mmol) in MeOH (1.62 mL), chilled in an ice bath. The reaction mixture was stirred at RT overnight and then evaporated. Boc-Leu-OH—H$_2$O (50 mg, 0.20 mmol), HATU (75 mg, 0.20 mmol), 1.8 mL DMF, and lastly, DIEA (125 μL, 0.72 mmol) were added. After stirring at RT for 5.5 h the mixture was concentrated in vacuo, and then partitioned between EtOAc and saturated aqueous NaHCO$_3$. The organic phase was washed twice with saturated aqueous NaCl, dried (Na$_2$SO$_4$), and concentrated in vacuo. Flash chromatography (silica, 3/1 isohexane—EtOAc) gave compound 9-3 as a white solid (86.3 mg, 85% yield).

Rf (TLC 1/1 isohexane—EtOAc) 0.54.

HPLC-MS: mass 571 [M+H]$^+$; R$_t$=3.75 min 96% (gradient 5 to 99% B in 3 min, then 100% B for 1.5 min)

Method—Flow: 0.8 mL/min, UV=210-400 nm, ACE C8 3×50 mm; Mobile phase A: 10 mM NH$_4$Ac in 90% H$_2$O, B: 10 mM NH$_4$Ac in 90% MeCN Step c)

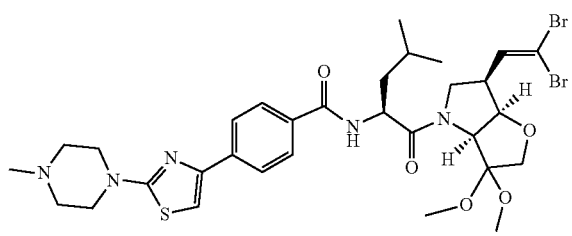 [SMILES: COC1(OC)CO[C@@H]2[C@H](C=C(Br)Br)CN(C(=O)[C@H](CC(C)C)NC(=O)c3ccc(-c4csc(N5CCN(C)CC5)n4)cc3)[C@@H]21]

Boc deprotection of compound 9-3 (86.3 mg, 0.15 mmol) was done as for 9-2 above to give the amine HCl salt. DMF (1.5 mL) was added to a mixture of the amine salt, 4-[2-(4-methyl-1-piperazinyl)-4-thiazolyl]-benzoic acid hydrobromide (65 mg, 0.17 mmol), and HATU (65 mg, 0.17 mmol) with cooling in an ice bath. DIEA (120 μL, 0.69 mmol) was added. After stirring at RT for 3 h, 20 mL EtOAc was added, and then the mixture was washed with 1M NaHCO$_3$ (10 mL), followed by saturated aqueous NaCl. The organic phase was dried (Na$_2$SO$_4$) and concentrated in vacuo to give crude product. Flash chromatography (silica, CH$_2$Cl$_2$-MeOH 100/1 to 100/4) gave the desired product as a pale yellow solid (65.7 mg, 58% yield).

HPLC-MS: mass 756 [M+H]$^+$; R$_t$=3.83 min (5 to 99% B in 3 min, then 100% B for 1.5 min) and R$_t$=4.07 min (30 to 80% B in 3 min, then 100% B for 1.5 min) 96% pure in two gradients Step d)

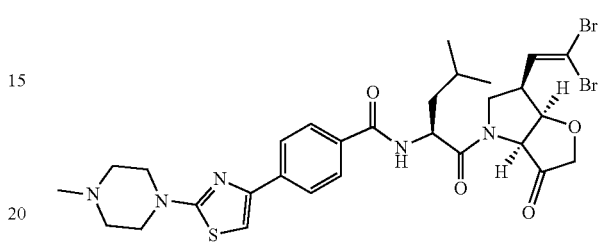

The ketal 9-4 (65.7 mg, 0.087 mmol) was stirred with 1.0 mL of 97.5/2.5 (v/v) TFA-H$_2$O for 4 h 20 min and then quenched with an aqueous suspension of NaHCO$_3$. The mixture was extracted with EtOAc. The organic phase was washed with saturated aqueous NaCl, dried (Na$_2$SO$_4$), and concentrated in vacuo. Purification by prep HPLC gave the ketone 9-5 as a white solid (12.6 mg).

1H NMR (500 MHz, CDCl$_3$) 2 rotomers, major: δ 7.90 and 7.81 (ABq, 4H, phenyl), 6.91-6.87 (2H, thiazole and NH), 6.67 (d, 1H, H̲C=CBr$_2$), 5.05 (td, 1H, Leu CHα), 4.85 (m, 1H, bicyclic bridge H̲CO), 4.74 (d, 1 H, bicyclic bridge H̲CN), 4.32 and 3.42 (1 H each, bicyclic NCH$_2$), 4.18 and 4.00 (ABq, 2 H, OCH$_2$), 3.59 (4H, piperazine CH̲$_2$N—thiazole), 3.25 (1 H, Br$_2$C=CH—CH̲), 2.56 (4H, piperazine CH$_2$NMe), 2.37 (s, 3H, NMe), 1.80—1.54 (d, 3H, CH̲$_2$CHMe$_2$),1.04 (d, 3H, CHM̲e$_2$), 0.94 (d, 3H, CHM̲e$_2$).

LC-UV/MS: Monoisotopic Molecular Mass 709.1 Da, >94% Purity (Column: ACE Cs 50×3.0 mm, 3 μm particles; Mobile phases A: 10 mM NH$_4$Ac, B: 10 mM NH4Ac in 90% MeCN; gradient: 30-70% B in 10 min followed by a wash for 2 min at 100% B; Flow:0.8 mL/min, Detection: UV @ 210-400 nm and ESI-MS)

EXAMPLE 1

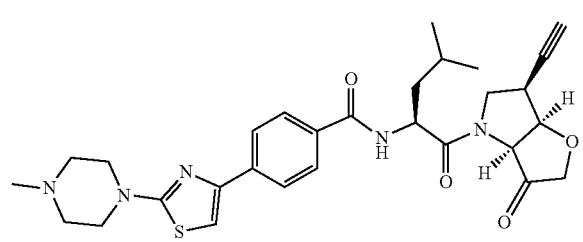 [SMILES: C#C[C@@H]1CN(C(=O)[C@H](CC(C)C)NC(=O)c2ccc(-c3csc(N4CCN(C)CC4)n3)cc2)[C@@H]2C(=O)CO[C@H]12]

N-[1-6-(ethynyl-3-oxo-hexahydro-furo[3,2-b]pyrrole-4-carbonyl)-3-methyl-butyl]-4-[2-(4-methyl-piperazin-1-yl)thiazol-4-yl]-benzamide Step a)

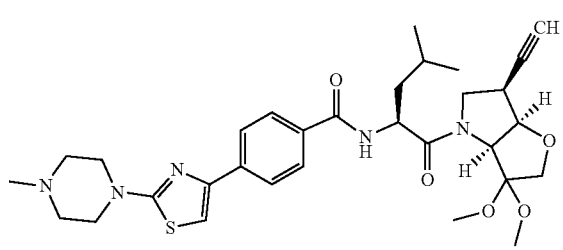 [SMILES: C#C[C@@H]1CN(C(=O)[C@H](CC(C)C)NC(=O)c2ccc(-c3csc(N4CCN(C)CC4)n3)cc2)[C@H]2[C@@H]1OCC2(OC)OC]

DMF (2 mL) was added to a mixture of 4-[2-(4-methyl-1-piperazinyl)-4-thiazolyl]-benzoic acid hydrobromide (73.9 mg, 0.19 mmol), the compound of Reference Example 5 (0.17 mmol), and HATU (73.4 mg, 0.19 mmol) with cooling in an ice bath. DIEA (0.12 mL, 0.69 mmol) was added. After stirring at RT for 2.5 h, the mixture was concentrated, redissolved in 20 mL EtOAc, and then washed with 10 mL saturated aqueous $NaHCO_3$. The aqueous phase was extracted with 10 mL EtOAc. The organic phases were combined, washed with saturated aqueous NaCl (2×15 mL), dried ($Na_2SO_4$), and evaporated to give crude product. Initial flash chromatography (silica 40-63 μm, 5-8% MeOH in EtOAc) gave purified material which was subjected to a second chromatography (YMC gel silica 6 nm S—50 μm, 1-5% MeOH in $CH_2Cl_2$) to give title compound as light yellow solids (50.1 mg, 49% yield).

HPLC-MS: mass 596 [M+H]$^+$, single peak, $R_t$=3.18 min (gradient 5 to 99% B in 3 min, then 100% B for 1.5 min)

Step b)

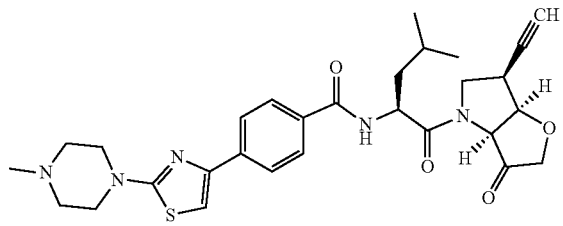 [SMILES: C#C[C@@H]1CN(C(=O)[C@H](CC(C)C)NC(=O)c2ccc(-c3csc(N4CCN(C)CC4)n3)cc2)[C@@H]2C(=O)CO[C@H]12]

The compound of step a) (50 mg, 0.0839 mmol) was dissolved in 10 mL of TFA: $H_2O$ (97.5: 2.5) and stirred for 4 hours. The solvent was pored into a separatory funnel, extracted with EtOAc and washed with saturated aqueous $NaHCO_3$. The organic phase was dried with $Na_2SO_4$, filtered and evaporated. The crude product was purified by semi-prep. HPLC on a XBrideg Phenyl 5 μm column with mobile phases A (90:10 $H_2O$: acetonitrile, 10 mM $NH_4Ac$) and B (10:90 $H_2O$:acetonitrile, 10 mM $NH_4Ac$) going from 25-60% B. The product was obtained as a white solid in 62% yield (29 mg). LRMS (M+H) 550.

$^1$H NMR (CDCl$_3$, 400 MHz): 0.95 (d, J=6.4, 3H), 1.03 (d, J=6.4, 3H), 1.57-2.10 (m 4H), 2.37 (s, 3H), 2.60 -2.54 (m, 4H), 3.17-3.26 (m, 1 H), 3.55-3.64 (m, 5H), 4.07 (d, J=17.1, 1 H), 4.27 (d, J=17.2, 1H), 4.50 (dd, J=7.8, 9.9, 1H), 4.77 (d, J=5.1, 1H), 4.91 (dd, J=4.6, 4.6, 1H), 4.97-5.06 (m, 1H), 6.85-6.91 (m, 2H), 7.79 (d, J=8.3, 2H), 7.89 (d, J=8.4, 3H).

EXAMPLE 2

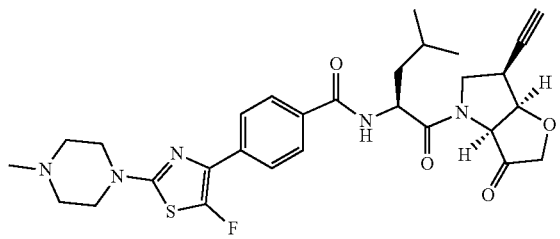 [SMILES: C#C[C@@H]1CN(C(=O)[C@H](CC(C)C)NC(=O)c2ccc(-c3nc(N4CCN(C)CC4)sc3F)cc2)[C@@H]2C(=O)CO[C@H]12]

N-[1-6-(ethynyl-3-oxo-hexahydro-furo[3,2-b]pyrrole-4-carbonyl)-3-methyl-butyl]-4-[5-fluoro-2-(4-methyl-piperazin-1-yl)thiazol-4-yl]-benzamide Step a)

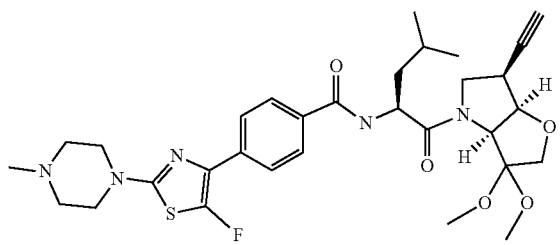 [SMILES: C#C[C@@H]1CN(C(=O)[C@H](CC(C)C)NC(=O)c2ccc(-c3nc(N4CCN(C)CC4)sc3F)cc2)[C@H]2[C@@H]1OCC2(OC)OC]

DMF (1.7 mL) was added to a mixture of 4-[5-fluoro-2-(4-methyl-1-piperazinyl)-4-thiazolyl]-benzoic acid hydrochloride (68.0 mg, 0.19 mmol), the compound of Reference Example 5 (0.17 mmol), and HATU (73.8 mg, 0.19 mmol) with cooling in an ice bath. DIEA (0.12 mL, 0.69 mmol) was added. After stirring at RT for 2.75 h, the mixture was treated as for Example 1 to give the crude fluorothiazole analogue. Flash chromatography (YMC gel silica, 1-3% MeOH in $CH_2Cl_2$) gave the title compound as light yellow solids (62.8 mg, 60% yield).

HPLC-MS: mass 614 [M+H]$^+$, single peak on UV, $R_t$=3.39 min (gradient 5 to 99% B in 3 min, then 100% B for 1.5 min)

Step b)

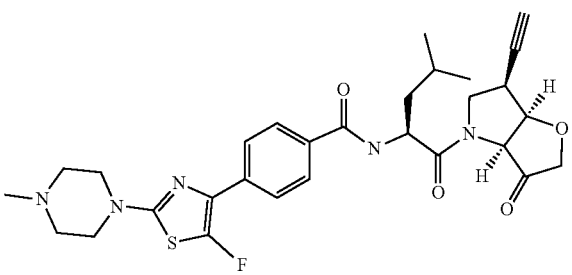 [SMILES: C#C[C@@H]1CN(C(=O)[C@H](CC(C)C)NC(=O)c2ccc(-c3nc(N4CCN(C)CC4)sc3F)cc2)[C@@H]2C(=O)CO[C@H]12]

The compound of step a) (63 mg, 0.102 mmol) was dissolved in 10 mL of TFA: H₂O (97.5: 2.5) and stirred for 4 hours. The solvent was pored into a separatory funnel, extracted with EtOAc and washed with sat. NaHCO₃₍aq₎. The organic phase was dried with Na₂SO₄, filtered and evaporated. The crude product was purified by semi-prep. HPLC on a XBrideg Phenyl 5 um column with mobile phases A (90:10 H₂O: acetonitrile, 10 mM NH₄Ac) and B (10:90 H₂O:acetonitrile, 10 mM NH₄Ac) going from 25-60% B. The product was obtained as a white solid in 46% yield (26 mg). LRMS (M+H) 568.

$^1$H NMR (CDCl₃, 400 MHz): 0.95 (d, J=6.4, 3H), 1.03 (d, J=6.4, 3H), 1.58-2.15 (m 4H), 2.37 (s, 3H), 2.61—2.48 (m, 4H), 3.18-3.25 (m, 1 H), 3.53-3.42 (m, 4H), 3.60 (t, J=10.5, 1 H), 4.07 (d, J=17.1, 1 H), 4.27 (d, J=17.2, 1 H), 4.56—4.46 (m, 1 H), 4.91 (t, J=4.5, 1 H), 4.96-5.06 (m, 1H), 6.87 (d, J=8.2, 1H), 7.81 (d, J=8.4, 2H), 7.90 (t, J=9.4, 2H).

EXAMPLE 3

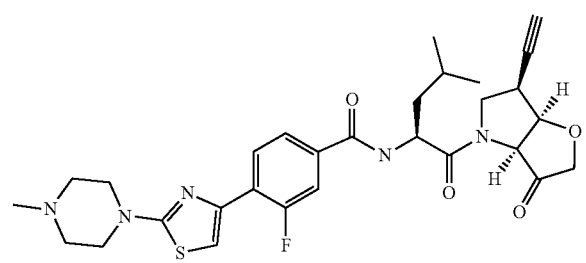 [SMILES: C#C[C@@H]1CN(C(=O)[C@H](CC(C)C)NC(=O)c2ccc(-c3csc(N4CCN(C)CC4)n3)c(F)c2)[C@@H]2C(=O)CO[C@H]12]

N-[1-6-(ethynyl-3-oxo-hexahydro-furo[3,2-b]pyrrole-4-carbonyl)-3-methyl-butyl]-3-fluoro-4-[2-(4-methyl-piperazin-1-yl)thiazol-4-yl]-benzamide Step a)

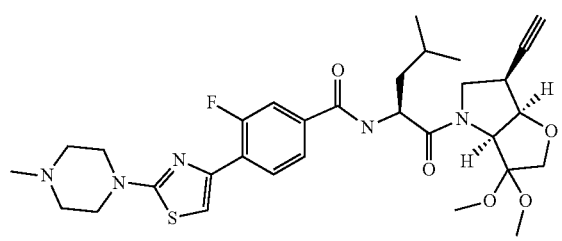 [SMILES: C#C[C@@H]1CN(C(=O)[C@H](CC(C)C)NC(=O)c2ccc(-c3csc(N4CCN(C)CC4)n3)c(F)c2)[C@H]2[C@@H]1OCC2(OC)OC]

DMF (1.7 mL) was added to a mixture of 3-fluoro-4-[2-(4-methyl-1-piperazinyl)-4-thiazolyl]-benzoic acid hydrochloride (68.9 mg, 0.19 mmol), the compound of Reference Example 5 (0.17 mmol), and HATU (80 mg, 0.21 mmol) with cooling in an ice bath. DIEA (0.12 mL, 0.69 mmol) was added. After stirring at RT for 3 h, the mixture was concentrated, redissolved in 30 mL EtOAc, washed successively with 15 mL saturated aqueous NaHCO₃ and then 30 mL saturated aqueous NaCl. The organic phase was dried (Na₂SO₄) and then evaporated. Flash chromatography (YMC gel silica, 1-3% MeOH in CH₂Cl₂) gave the title compound as off-white solids (72.4 mg, 70% yield).

HPLC-MS: mass 614 [M+H]⁺, $R_f$=3.46 min (gradient 5 to 99% B in 3 min, then 100% B for 1.5 min Step b)

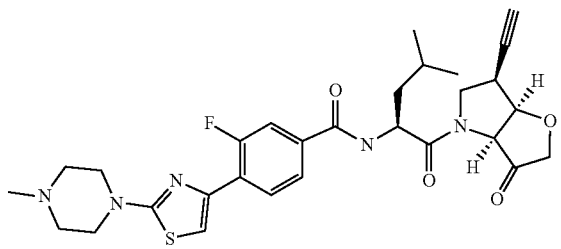 [SMILES: C#C[C@@H]1CN(C(=O)[C@H](CC(C)C)NC(=O)c2ccc(-c3csc(N4CCN(C)CC4)n3)c(F)c2)[C@@H]2C(=O)CO[C@H]12]

The ketal of step a) (67 mg, 0.11 mmol) was stirred with 1.10 mL of 97.5/2.5 (v/v) TFA-H₂O for 2 h and then concentrated. The mixture was diluted with EtOAc (10 mL), washed with saturated aqueous NaHCO₃ (5 mL), followed by saturated aqueous NaCl (2×5 mL), dried (Na₂SO₄), and evaporated. The crude material was dissolved in 2 ml MeCN and 1 mL H₂O, and 0.9 ml of this solution was purified by prep HPLC to give the ketone of the title compound as white solids (8.2 mg).

1H NMR (500 MHz, CDCl₃) 2 rotomers δ 8.22 (m, 1 H, Ph), 7.63-7.55 (m, 2H, Ph), 7.21 (m, 1 H, thiazol), major 6.91 and minor 6.87 (d, 1 H, J=8.0 and 7.5 Hz, NHC═O), minor 5.05 and major 5.00 (m, 1 H), 4.93 (m, 1 H), 4.79 (d, 1 H, J=5.0 Hz), 4.48 (dd, 1 H, J=10.2, 7.7 Hz), 4.28 and 4.09 (ABq, 1H each), 3.64-3.59 (m, 5H), 3.23 (m, 1 H, HC—C≡CH), 2.58 (m, 4H), 2.38 (s, 3H, NMe), 2.35 (d, 1 H, J=2.0 Hz, C≡CH), 1.78-1.59 (m, 3H), 1.04 (d, 3H, J=6.0 Hz), 0.96 (d, 3H, J=6.5 Hz).

LC-UV/MS: Monoisotopic Molecular Mass 567.2 Da, 97.6% Purity (Column: ACE C₈ 50×3.0 mm, 3 μm particles; Mobile phases A: 10 mM NH₄Ac, B: 10 mM NH₄Ac in 90% MeCN; gradient: 20-100% B in10 min followed by a wash for 2 min at 100%; Flow:0.8 mL/min, Detection: UV @ 210-400 nm and ESI-MS)

EXAMPLE 4

N-[1-6-(dimethylvinyl-3-oxo-hexahydro-furo[3,2-b]pyrrole-4-carbonyl)-3-methyl-butyl]-4-[5-fluoro-2-(4-methyl-piperazin-1-yl)thiazol-4-yl]-benzamide

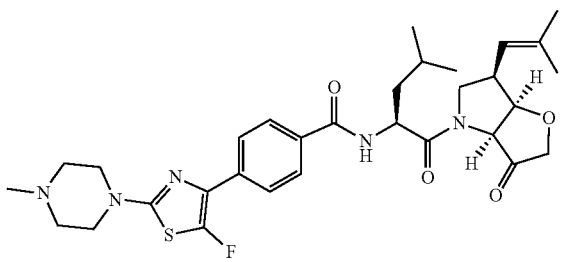 [SMILES: CC(C)=C[C@@H]1CN(C(=O)[C@H](CC(C)C)NC(=O)c2ccc(-c3nc(N4CCN(C)CC4)sc3F)cc2)[C@@H]2C(=O)CO[C@H]12]

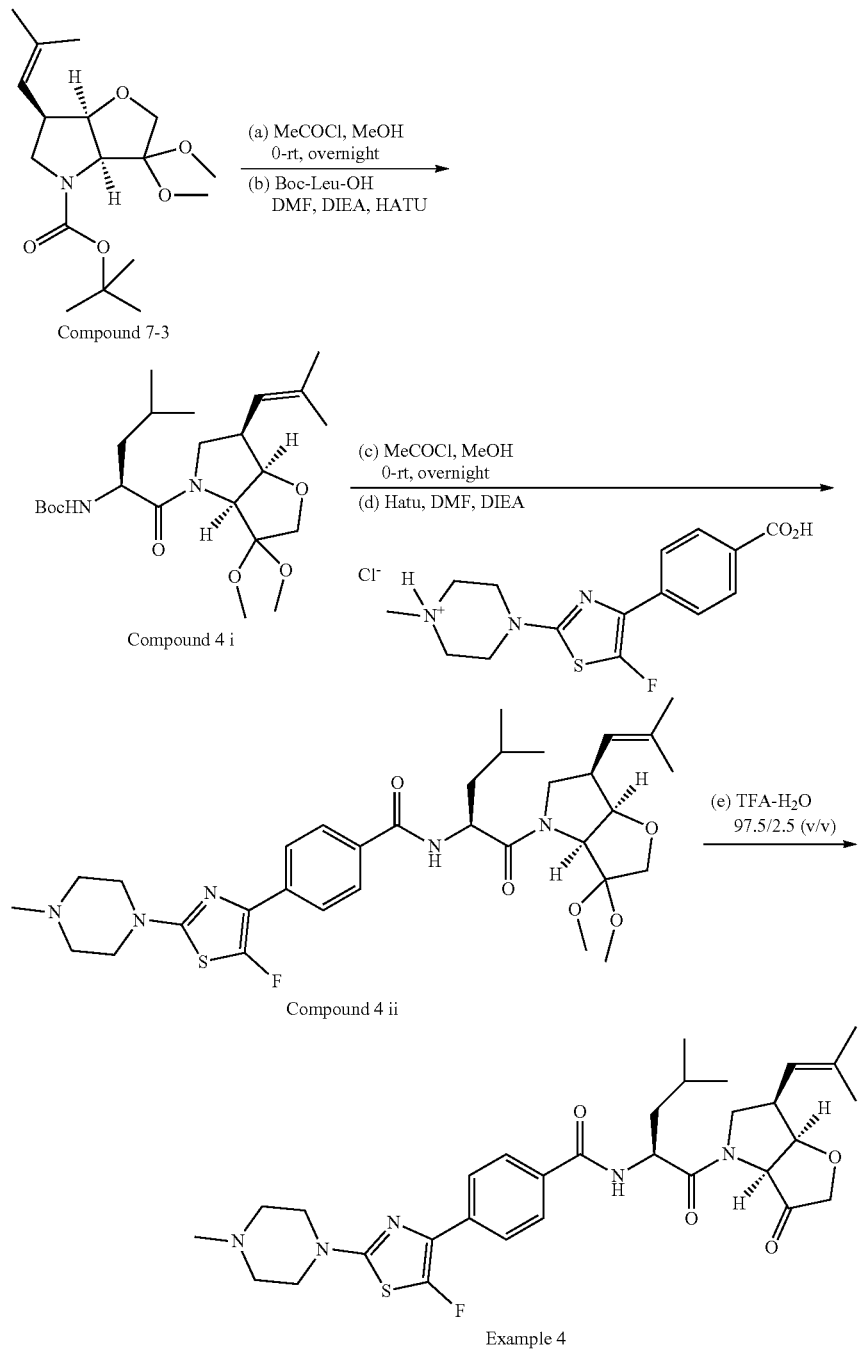

Acetyl chloride (0.3 mL) was added dropwise to an ice-cooled solution of compound 7-3 (103.4 mg, 0.316 mmol) (see reference example 7) in methanol (2.9 mL). The solution was stirred at rt overnight, and then concentrated in vacuo, coevaporated twice with $CH_2Cl_2$, and dried under vacuum. Boc-L-leucine-$H_2O$ (96.2 mg, 0.386 mmol) and HATU (143 mg, 0.376 mmol) were added and the mixture was cooled in an ice bath. DMF (3.2 mL), followed by DIEA (220 μL, 1.26 mmol) were added. The resulting solution was stirred at rt for 6 h. The reaction mixture was concentrated in vacuo, redissolved in EtOAc (15 mL), and washed successively with saturated aqueous $NaHCO_3$ (10 mL) and saturated aqueous NaCl (10 mL). The organic phase was dried ($Na_2SO_4$) and then concentrated in vacuo to give the crude material. Flash column chromatography (silica, 2/1 isohexane-EtOAc) gave compound 4i as white solids (127.8 mg, 92% yield).

TLC $R_f$=0.56 (1/1 isohexane—EtOAc)

LC-UV/MS Rt=1.98 min (single peak), mass 441 [M+H]$^+$ (gradient 70 to 99% B in 3 min, then 100% B for 1.5 min (Method—Flow 0.8 mL/min, UV=210-400 nm, Phenomenex Gemini—NX 3 μm C18 110 Å 50×3.0 mm, Mobile phases A: 10 mM NH$_4$Ac in H$_2$O, B: 10 mM NH$_4$Ac in 90/10 MeCN—H$_2$O)

Compound 4-i (127.8 mg, 0.290 mmol) was deprotected as above using MeOH (2.7 mL) and acetyl chloride (0.30 mL). The coupling of the resulting amine HCl salt (half of material, 0.145 mmol) with 4-[5-fluoro-2-(4-methyl-1-piperazinyl)-4-thiazolyl]-benzoic acid hydrochloride (67.4 mg, 0.19 mmol) was done similarly as the Boc-Leu-OH coupling step, in DMF (2.0 mL) with HATU (69 mg, 0.18 mmol) and DIEA (115 μL, 0.66 mmol) for 3.5 h. After flash column chromatography of the crude product (silica, 2-5% MeOH in CH$_2$Cl$_2$), compound 4-ii was obtained as pale yellow solids (48.3 mg, 52% yield).

TLC Rf=0.5 (9/1 CH$_2$Cl$_2$_MeOH)

LC-UV/MS Rt=2.41 min, 95q % pure, mass 644 [M+H]$^+$ (gradient 70 to 99% B in 3 min, then 100% B for 1.5 min To an ice-cooled solution of the ketal 4-ii (41.3 mg, 0.064 mmol) in CH$_2$Cl$_2$ (0.3 mL) was added dropwise 0.65 ml of a solution of TFA-water (97.5/2.5 v/v). The reaction mixture was stirred for 30 min at rt, and then replaced in an ice bath and quenched with saturated aqueous NaHCO$_3$ (10 mL). The mixture was extracted twice with EtOAc (20 mL, 10 mL). The organic phases were combined, washed with saturated aqueous NaCl (10 mL), dried (Na$_2$SO$_4$), and concentrated in vacuo. Purification by prep HPLC gave the final title compound.

LC-UV/MS Rt =6.5 and 7.5 min (hydrate and ketone), 98% pure, monoisotopic molecular mass 597.3 Da (Method—Flow 0.8 mL/min; UV=210-400 nm and ESI-MS; Phenomenex Gemini-NX C18 50×3.0 mm, 3 μm particles; Mobile phases A: 5 mM NH$_4$Ac in H$_2$O, B: 5 mM NH$_4$Ac in MeCN, gradient 20-99% B in 10 min followed by a wash for 2 min at 100% B)

EXAMPLE 5

N-[1-(6-ethynyl-3-oxo-hexahydro-furo[3,2-b]pyrrol-4-yl)-1-cyclopentyl-2-oxo-ethyl]-4-[5-fluoro-2-(4-methyl-piperazin-1-yl)-thiazol-4-yl]-benzamide Step a)

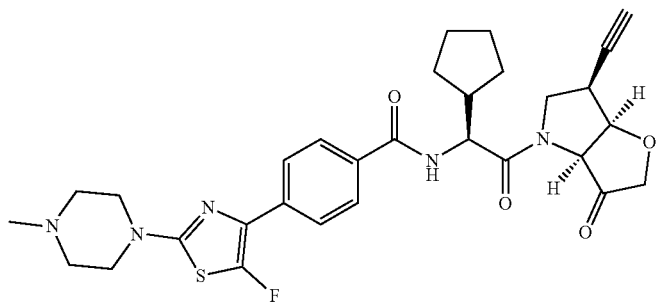

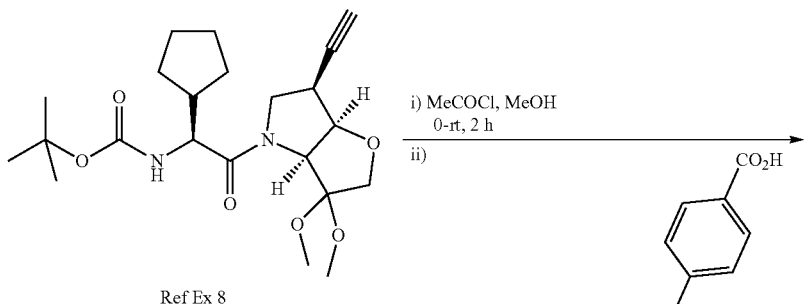

Ref Ex 8

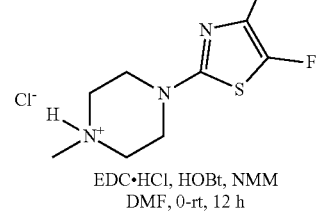

EDC·HCl, HOBt, NMM
DMF, 0-rt, 12 h

-continued

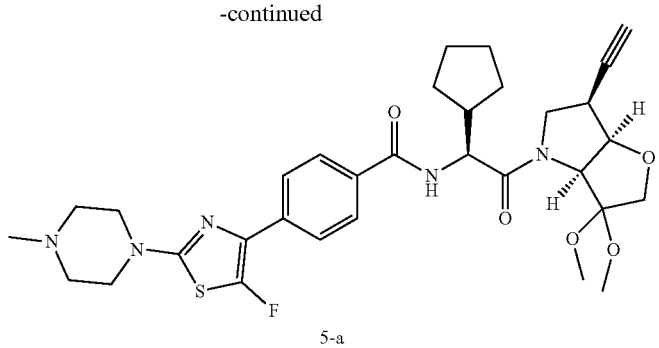

5-a

The reaction was carried out in a similar way as reported in case of Example 3 but using the P1-P2 building block of reference example 8 (0.14 g, 0.33 mmol) in dry MeOH (15 mL) and acetyl chloride (0.5 mL) was used to get the Boc-deprotected amine which was further treated with the HCl salt (0.132 g, 0.33 mmol), HOBt (0.04 g, 0.3 mmol), EDC.HCl (0.117 g, 0.61 mmol) and NMM (0.11 mL, 1.0 mmol) in dry DMF (10 mL) to get the pure compound 5-a [0.05 g, yield 26 %]. TLC system: CHCl$_3$:MeOH 9.5:0.5 v/v, R$_f$=0.25.

Step b)

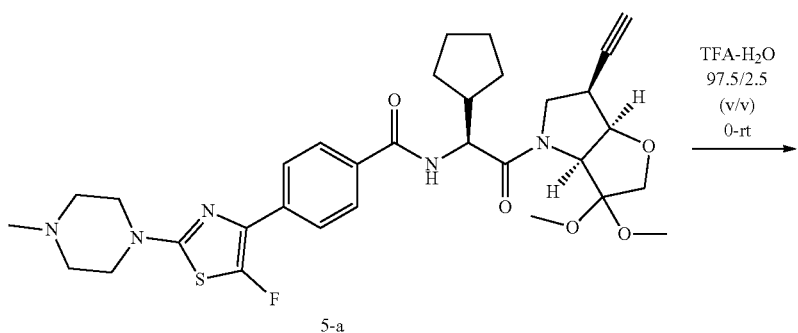

5-a

TFA-H$_2$O
97.5/2.5
(v/v)
0-rt

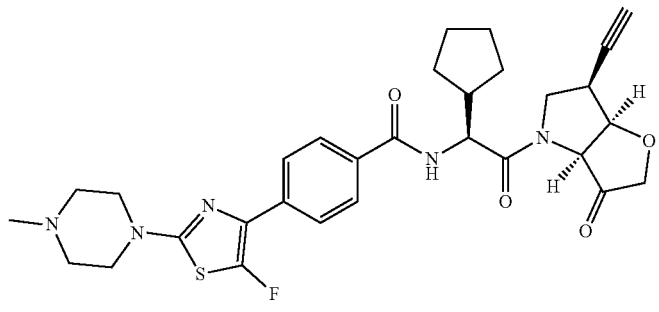

Example 5

Deprotection of ketal 5-a (40.5 mg, 0.065 mmol) to the title ketone was conducted as for compound 3 using 0.65 mL of the TFA-water solution, with reaction at rt for 2 h 15 min. Purification by prep HPLC gave 11 as pale yellow solids (14.75 mg).

LC-UV/MS Rt=5.3 and 6.0 min, (hydrate and ketone), 96.7% pure, monoisotopic molecular mass 579.2 Da (Method—Flow 0.8 mUmin; UV=210-400 nm and ESI-MS; Phenomenex Gemini-NX C18 50×3.0 mm, 3 μm particles; Mobile phases A: 5 mM NH$_4$Ac, B: 5 mM NH4Ac in MeCN, gradient 20-99% B in 10 min followed by a wash for 2 min at 100%B)

Biological Examples

Determination of Cathepsin K Proteolytic Catalytic Activity

Convenient assays for cathepsin K are carried out using human recombinant enzyme, such as that described in PDB. ID BC016058 standard; mRNA; HUM; 1699 BP.

DE Homo sapiens cathepsin K (pycnodysostosis), mRNA (cDNA clone MGC:23107

RX MEDLINE;. RX PUBMED; 12477932.

DR RZPD; IRALp962G1234.

DR SWISS-PROT; P43235;

The recombinant cathepsin K can be expressed in a variety of commercially available expression systems including E coli, Pichia and Baculovirus systems. The purified enzyme is activated by removal of the prosequence by conventional methods.

Standard assay conditions for the determination of kinetic constants used a fluorogenic peptide substrate, typically H-D-Ala-Leu-Lys-AMC, and were determined in either 100 mM Mes/Tris, pH 7.0 containing 1 mM EDTA and 10 mM 2-mercaptoethanol or 100 mMNa phosphate, imM EDTA, 0.1% PEG4000 pH 6.5 or 100 mM Na acetate, pH 5.5 containing 5 mM EDTA and 20 mM cysteine, in each case optionally with 1M DTT as stabiliser. The enzyme concentration used was 5 nM. The stock substrate solution was prepared at 10 mM in DMSO. Screens were carried out at a fixed substrate concentration of 60 µM and detailed kinetic studies with doubling dilutions of substrate from 250 µM. The total DMSO concentration in the assay was kept below 3%. All assays were conducted at ambient temperature. Product fluorescence (excitation at 390 nm, emission at 460 nm) was monitored with a Labsystems Fluoroskan Ascent fluorescent plate reader. Product progress curves were generated over 15 minutes following generation of AMC product.

Cathepsin S Ki Determination

The assay uses baculovirus-expressed human cathepsin S and the boc-Val-Leu-Lys-AMC fluorescent substrate available from Bachem in a 384 well plate format, in which 7 test compounds can be tested in parallel with a positive control comprising a known cathepsin S inhibitor comparator.

Substrate Dilutions

280 µl/well of 12.5% DMSO are added to rows B—H of two columns of a 96 deep well polypropylene plate. 70 µl/well of substrate is added to row A. 2×250 µl/well of assay buffer (100 mM Na phosphate, 100 mM NaCl, pH 6.5) is added to row A, mixed, and double diluted down the plate to row H.

Inhibitor Dilutions

100 µl/well of assay buffer is added to columns 2-5 and 7-12 of 4 rows of a 96 well V bottom polypropylene plate. 200 µl/well of assay buffer is added to columns 1 and 6.

The first test compound prepared in DMSO is added to column 1 of the top row, typically at a volume to provide between 10 and 30 times the initially determined rough K. The rough Ki is calculated from a preliminary run in which 10 µl/well of 1mM boc-VLK-AMC (1/10 dilution of 10 mM stock in DMSO diluted into assay buffer) is dispensed to rows B to H and 20 µl/well to row A of a 96 well Microfluor™ plate. 2 µl of each 10 mM test compound is added to a separate well on row A, columns 1-10. Add 90 µl assay buffer containing 1 mM DTT and 2 nM cathepsin S to each well of rows B-H and 180 µl to row A. Mix row A using a multichannel pipette and double dilute to row G. Mix row H and read in the fluorescent spectrophotometer. The readings are Prism data fitted to the competitive inhibition equation, setting S=100 µM and $K_M$=100 µM to obtain an estimate of the $K_i$, up to a maximum of 100 µM.

The second test compound is added to column 6 of the top row, the third to column 1 of the second row etc. Add 1 µl of comparator to column 6 of the bottom row. Mix column 1 and double dilute to column 5. Mix column 6 and double dilute to column 10.

Using an 8-channel multistepping pipette set to 5×10 µl, distribute 10 µl/well of substrate to the 384 well assay plate. Distribute the first column of the substrate dilution plate to all columns of the assay plate starting at row A. The tip spacing of the multichannel pipette will correctly skip alternate rows. Distribute the second column to all columns starting at row B.

Using a 12-channel multistepping pipette set to 4×10 µl, distribute 10 µl/well of inhibitor to the 384 well assay plate. Distribute the first row of the inhibitor dilution plate to alternate rows of the assay plate starting at A1. The tip spacing of the multichannel pipette will correctly skip alternate columns. Similarly, distribute the second, third and fourth rows to alternate rows and columns starting at A2, B1 and B2 respectively.

Mix 20 ml assay buffer and 20 µl 1 M DTT. Add sufficient cathepsin S to give 2 nM final concentration.

Using the a distributor such as a Multidrop 384, add 30 µl/well to all wells of the assay plate and read in fluorescent spectrophotomoter such as an Ascent.

Fluorescent readings, (excitation and emission wavelengths 390 nm and 460 nm respectively, set using bandpass filters) reflecting the extent of enzyme cleavage of the fluorescent substrate, notwithstanding the inhibitor, are linear rate fitted for each well.

Fitted rates for all wells for each inhibitor are fitted to the competitive inhibition equation using SigmaPlot 2000 to determine V, Km and Ki values.

Cathepsin L Ki

The procedure above with the following amendments is used for the determination of Ki for cathepsin L.

The enzyme is commercially available human cathepsin L (for example Calbiochem). The substrate is H-D-Val-Leu-Lys-AMC available from Bahcem. The assay buffer is 100mM sodium acetate 1 mM EDTA, pH5.5) The DMSO stock (10 mM in 100% DMSO) is diluted to 10% in assay buffer. Enzyme is prepared at 5 nM concentration in assay buffer plus 1 mM dithiothreitol just before use. 2 ul of 10 mM inhibitor made up in 100% DMSO is dispensed into row A. 10 µl of 50 µM substrate (=1/200 dilution of 10 mM stock in DMSO,diluted in assay buffer)

Inhibition Studies

Potential inhibitors are screened using the above assay with variable concentrations of test compound. Reactions were initiated by addition of enzyme to buffered solutions of substrate and inhibitor. $K_i$ values were calculated according to equation 1.

$$v_0 = \frac{VS}{K_M\left(1 + \frac{I}{K_i}\right) + S} \quad (1)$$

where $v_o$ is the velocity of the reaction, V is the maximal velocity, S is the concentration of substrate with Michaelis constant of $K_M$, and I is the concentration of inhibitor.

Results are presented as:

A under 50 nanomolar
B 50-500 nanomolar
C 501-1000 nanomolar
D 1001—5000 nanomolar
E 5001 -10 000 nanomolar
F in excess of 10 000 nanomolar

TABLE 1

| Example | Test Number | Ki cathepsin K | Ki cathepsin S | Ki cathepsin L |
|---|---|---|---|---|
| 1 | Test 1 | A | F | D |
| 2 | Test 1 | A | F | D |
| 3 | Test 1 | A | F | C |
| 1 | Test 2 | 1.6 nM | 25 000 nM | 2000 nM |
| 2 | Test 2 | 1.1 nM | 21 000 nM | 1700 nM |
| 3 | Test 2 | 4 nM | 22 000 nm | 1400 nM |
| 4 | — | 2.7 nM | 14 500 nM | 300 nM |
| 5 | — | 0.6 nM | 2 900 nM | 1 170 nm |
| Ref Ex 9 | — | 2.6 nM | 6 100 nM | NA |

The compounds of formula II are thus potent inhibitors of cathepsin K and yet selective over the closely related cathepsin S and L. The compound of reference example 9 provides confidence that the corresponding difluorovinyl compounds are also active and selective

Metabolic Stability

Compounds of the invention and the indicated comparative examples were tested for metabolic stability in a cytosol assay in which the compounds were incubated with commercially available human hepatic cytosol fractions and the disappearance of the compound monitored by HPLC or LC/MS. Pooled human liver cytosol fractions are less likely to represent outlier individuals than blood from a single individual and can be stored frozen, unlike whole blood. The cytosol assay thus provides a consistent assay testbed as a guide to the stability of a compound in the in vivo environment, such as when exposed to whole blood.

In short, test compounds (2 μM) are incubated in pooled human liver cytosol (Xenotech LLC Lenexa US, 1 mg/mL protein in 0.1 M phosphate buffer, pH 7.4) at 37° centigrade over a one hour period. The incubations are initiated by the addition of 1mM NADPH co-factor. Timed sub-samples were taken at 0, 20, 40 and 60 minutes and "crash precipitated" by the addition of 3 volumes of ice-cold acetonitrile. The samples were centrifuged at reduced temperature and the supernatants were separated and analyzed by LC-MS-MS.

Alternatively, an analogous stability assay is carried out in human or monkey whole blood and/or commercially available liver microsomes, such as XEN 025.

TABLE 2

| Example | Structure | CLint whole blood ul/min/mg | CLint HLM ul/min/mg |
|---|---|---|---|
| comparative example | (structure shown) | 9 | 49 |
| Example 1 | (structure shown) | 3 | 16 |

Comparative Example 1 represents a compound bearing a carbon-carbon bond at the 6 position within the scope of WO2008/007107 cited above. It was prepared in a facile manner from compound 1d (scheme 1). Hence with the exocyclic alkene 1d in hand, stereoselective hydrogenation of the alkene with Adams' catalyst (platinum dioxide) in ethyl acetate under a hydrogen atmosphere, proceeded with syn addition of hydrogen. This hydrogenation afforded essentially one product, namely the C-6 methyl isomer (LCMS [M+H]=288 found) with R-stereochemistry in good yield. The facial selectivity seen here for the hydrogenation step, is similar to that reported previously in the literature for a closely related bicyclic structure (Srinivas et al, Synlett, 1999, 555-556). The thus prepared building block was deprotected, elongated and oxidised to the active keto form as for the compounds of the invention exemplified above.

It will be apparent from Comparative Example 1 that a methyl group at the 6 position provides a compound with whole blood CLint value of 9 micrograms/minute/mg, representing an estimated whole blood half life of little over an hour. In contrast acetylene provided a Clint value of 3, which represents a calculated whole blood half life approaching 4 hours. Note also that the HLM microsome clearances (representing the contribution of the liver to metabolism of the respective compounds) is significantly higher for the 6-methyl species than for the compound of the invention, which will further accentuate the better stability of the present invention. Improved stability in vivo allows for a better distribution of the compound in the body throughout the day, notwithstanding QD or BID dosing. This is particularly important for indications such as osteoporosis where diurnal variation is significant.

Permeability

This experiment measures transport of inhibitors through the cells of the human gastroenteric canal. The assay uses the well known Caco-2 cells with a passage number between 40 and 60.

Apical to Basolateral Transport

Generally every compound will be tested in 2-4 wells. The basolateral and the apical wells will contain 1.5 mL and 0.4 mL transport buffer (TB), respectively, and the standard concentration of the tested substances is 10 µM. Furthermore all test solutions and buffers will contain 1% DMSO. Prior to the experiment the transport plates are pre-coated with culture medium containing 10% serum for 30 minutes to avoid nonspecific binding to plastic material. After 21 to 28 days in culture on filter supports the cells are ready for permeability experiments.

Transport plate no 1 comprises 3 rows of 4 wells each. Row 1 is denoted Wash, row 2 "30 minutes" and row 3 "60 minutes". Transport plate no 2 comprises 3 rows of 4 wells, one denoted row 4 "90 minutes", row 5 "120 minutes and the remaining row unassigned.

The culture medium from the apical wells is removed and the inserts are transferred to a wash row (No. 1) in a transport plate (plate no. 1) out of 2 plates without inserts, which have already been prepared with 1.5 mL transport buffer (HBSS, 25 mM HEPES, pH 7.4) in rows 1 to 5. In ASB screening the TB in basolateral well also contains 1% Bovine Serum Albumin.

0.5 mL transport buffer (HBSS, 25 mM MES, pH 6.5) is added to the inserts and the cell monolayers equilibrated in the transport buffer system for 30 minutes at 37° C. in a polymix shaker. After being equilibrated to the buffer system the Transepithelial electrical resistance value (TEER) is measured in each well by an EVOM chop stick instrument. The TEER values are usually between 400 to 1000Ω per well (depends on passage number used).

The transport buffer (TB, pH 6.5) is removed from the apical side and the insert is transferred to the 30 minutes row (No. 2) and fresh 425 µL TB (pH 6.5), including the test substance is added to the apical (donor) well. The plates are incubated in a polymix shaker at 37° C. with a low shaking velocity of approximately 150 to 300 rpm.

After 30 minutes incubation in row 2 the inserts will be moved to new pre-warmed basolateral (receiver) wells every 30 minutes; row 3 (60 minutes), 4 (90 minutes) and 5 (120 minutes).

25 µL samples will be taken from the apical solution after ~2 minutes and at the end of the experiment. These samples represent donor samples from the start and the end of the experiment.

300 µL will be taken from the basolateral (receiver) wells at each scheduled time point and the post value of TEER is measured at the end the experiment. To all collected samples acetonitrile will be added to a final concentration of 50% in the samples. The collected samples will be stored at ~20° C. until analysis by HPLC or LC-MS.

Basolateral to Apical Transport

Generally every compound will be tested in 2-4 wells. The basolateral and the apical wells will contain 1.55 mL and 0.4 mL TB, respectively, and the standard concentration of the tested substances is 10 µM. Furthermore all test solutions and buffers will contain 1% DMSO. Prior to the experiment the transport plates are precoated with culture medium containing 10% serum for 30 minutes to avoid nonspecific binding to plastic material.

After 21 to 28 days in culture on filter supports the cells are ready for permeability experiments. The culture medium from the apical wells are removed and the inserts are transferred to a wash row (No. 1) in a new plate without inserts (Transport plate).

The transport plate comprises 3 rows of 4 wells. Row 1 is denoted "wash" and row 3 is the "experimental row". The transport plate has previously been prepared with 1.5 mL TB (pH 7.4) in wash row No. 1 and with 1.55 mL TB (pH 7.4), including the test substance, in experimental row No. 3 (donor side).

0.5 mL transport buffer (HBSS, 25 mM MES, pH 6.5) is added to the inserts in row No. 1 and the cell monolayers are equilibrated in the transport buffer system for 30 minutes, 37° C. in a polymix shaker. After being equilibrated to the buffer system the TEER value is measured in each well by an EVOM chop stick instrument.

The transport buffer (TB, pH 6.5) is removed from the apical side and the insert is transferred to row 3 and 400 µL fresh TB, pH 6.5 is added to the inserts. After 30 minutes 250 µL is withdrawn from the apical (receiver) well and replaced by fresh transport buffer. Thereafter 250 µL samples will be withdrawn and replaced by fresh transport buffer every 30 minutes until the end of the experiment at 120 minutes, and finally a post value of TEER is measured at the end of the experiment. A 25 µL samples will be taken from the basolateral (donor) compartment after ~2 minutes and at the end of the experiment. These samples represent donor samples from the start and the end of the experiment.

To all collected samples acetonitrile will be added to a final concentration of 50% in the samples. The collected samples will be stored at −20° C. until analysis by HPLC or LC-MS.

Calculation

Determination of the cumulative fraction absorbed, $FA_{cum}$, versus time. $FA_{cum}$ is calculated from:

$$FA_{cum} = \sum_i \frac{C_{Ri}}{C_{Di}}$$

Where $C_{Ri}$ is the receiver concentration at the end of the interval i and $C_{Di}$ is the donor concentration at the beginning of interval i. A linear relationship should be obtained.

The determination of permeability coefficients ($P_{app}$, cm/s) are calculated from:

$$P_{app} = \frac{(k \cdot V_R)}{(A \cdot 60)}$$

where k is the transport rate (min⁻¹) defined as the slope obtained by linear regression of cumulative fraction absorbed ($FA_{cum}$) as a function of time (min), $V_R$ is the volume in the receiver chamber (mL), and A is the area of the filter (cm²).

Reference Compounds

| Category of absorption in man | Markers | % absorption in man |
|---|---|---|
| PASSIVE TRANSPORT | | |
| Low (0-20%) | Mannitol | 16 |
| | Methotrexate | 20 |
| Moderate (21-75%) | Acyclovir | 30 |
| High (76-100%) | Propranolol | 90 |
| | Caffeine | 100 |
| ACTIVE TRANSPORT | | |
| Amino acid transporter | L-Phenylalanine | 100 |
| ACTIVE EFFLUX | | |
| PGP-MDR1 | Digoxin | 30 |

Greater permeability through the gastrointestinal tissue is advantageous in that it allows for the use of a smaller dose to achieve similar levels of exposure to a less permeable compound administered in a higher dose. A low dose is advantageous in that minimises the cost of goods for a daily dose, which is a crucial parameter in a drug which is taken for protracted time periods.

The compound of Example 2 exhibited a $Pa_{pp}$ value of $9.1 \times 10^{-6}$ cm/sec in the Caco-2 assay, whereas the prior art compound of Example 2 of WO2008 007107 exhibited a $P_{app}$ value of $2.7 \times 10^{-6}$ cm/sec in a side-by-side assay run. In this assay system the arguably prior art compound N-((S)-1-((3aS, 6R, 6aS)-6-methoxy-oxodihydro-2H-furo[3,2-b]pyrrol-4(5H, 6H, 6aH)-yl)-4-methyl-oxopentan-2-yl)-4-(2-(4-methylpiperazine-1-yl)thiazol-4-yl)benzamide which is recited at page 33 of WO2008/007107 (but whose preparation is not disclosed) exhibits a $p_{app}$ value of $0.9 \times 10^{-6}$ cm/sec.

As a rule of thumb, a $p_{app}$ value around 2 represents an in vivo absorption of only 10-30% whereas a $p_{app}$ value approaching 10 will generally represent complete absorption.

The substantial difference in $P_{app}$ values between Example 2 and the abovementioned prior art Example 2 of WO2008 007107 correlates well with in vivo mouse PK experiments, as illustrated in FIG. 1. The respective compounds were orally administered (60 μmol/kg in a conventional 1% Methocel A4C vehicle. As seen clearly in FIG. 1, the in vivo exposure (whether measured as $C_{max}$ or AUC) was very much greater for the compound of the invention than the the prior art compound (Example 2 of WO2008 007107). Note that the graph has a logarithmic scale Mutagenicity The mutagenic potential of compounds is conveniently tested in the Ames Test, typically carried out in a variety of bacterial strains such as Salmonella typhimurium TA100, TA102, TA 1535, TA 1537 with and without liver S9 fraction activation, for example at 30, 300 and 3000 ug/plate concentrations.

Ames testing is readily available at a number of CROs around the world.

| Abbreviations | | | |
|---|---|---|---|
| DMF | dimethylformamide | DCM | dichloromethane |
| TBDMS | tert-butyldimethylsilyl | RT | room temperature |
| THF | tetrahydrofuran | Ac | acetyl |
| TLC | thin layer chromatography | DMAP | dimethylaminopyridine |
| EtOAc | ethyl acetate | uM | micromolar |

All references referred to in this application, including patents and patent applications, are incorporated herein by reference to the fullest extent possible.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

The invention claimed is:

1. A compound of the formula:

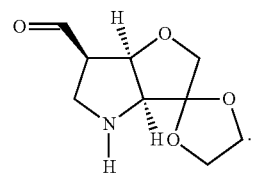 [SMILES: O=C[C@@H]1CN[C@H]2[C@@H]1OCC21OCCO1 ; "."]

* * * * *